(12) United States Patent
Lapidot et al.

(10) Patent No.: US 8,367,057 B2
(45) Date of Patent: Feb. 5, 2013

(54) STEM CELLS SUITABLE FOR TRANSPLANTATION, THEIR PREPARATION AND PHARMACEUTICAL COMPOSITIONS COMPRISING THEM

(75) Inventors: Tsvee Lapidot, Ness Ziona (IL); Joy Kahn, Ramat Beit Shemesh (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/031,466

(22) Filed: Feb. 21, 2011

(65) Prior Publication Data

US 2011/0268712 A1 Nov. 3, 2011

Related U.S. Application Data

(63) Continuation of application No. 10/578,291, filed as application No. PCT/IL2004/001018 on Nov. 8, 2004.

(30) Foreign Application Priority Data

Nov. 13, 2003 (IL) .......................... 158868

(51) Int. Cl.
*A61K 35/12* (2006.01)
*C12N 5/10* (2006.01)
*C12N 15/85* (2006.01)
*A61P 43/00* (2006.01)

(52) U.S. Cl. .................... 424/93.21; 435/325; 435/372; 435/455

(58) Field of Classification Search ............... None
See application file for complete search history.

(56) References Cited

U.S. PATENT DOCUMENTS

| | | | |
|---|---|---|---|
| 4,588,585 A | 5/1986 | Mark et al. |
| 4,737,462 A | 4/1988 | Mark et al. |
| 4,873,316 A | 10/1989 | Meade et al. |
| 4,879,111 A | 11/1989 | Chong |
| 4,904,584 A | 2/1990 | Shaw |
| 4,959,314 A | 9/1990 | Mark et al. |
| 4,965,195 A | 10/1990 | Namen et al. |
| 5,017,691 A | 5/1991 | Lee et al. |
| RE33,653 E | 7/1991 | Mark et al. |
| 5,116,743 A | 5/1992 | Goto et al. |
| 5,486,359 A | 1/1996 | Caplan et al. |
| 5,837,539 A | 11/1998 | Caplan et al. |
| 5,843,780 A | 12/1998 | Thomson |
| 5,928,638 A | 7/1999 | Uchida et al. |
| 6,090,622 A | 7/2000 | Gearhart et al. |
| 6,132,708 A | 10/2000 | Grompe |
| 6,143,292 A | 11/2000 | Slavin |
| 6,184,035 B1 | 2/2001 | Csete et al. |
| 6,248,587 B1 | 6/2001 | Rodgers et al. |
| 6,258,597 B1 | 7/2001 | Bachovchin et al. |
| 6,280,718 B1 | 8/2001 | Kaufman et al. |
| 6,326,198 B1 | 12/2001 | Emerson et al. |
| 6,383,481 B1 | 5/2002 | Ikehara et al. |
| 6,436,704 B1 | 8/2002 | Roberts et al. |
| 6,447,765 B1 | 9/2002 | Horwitz |
| 6,447,766 B1 | 9/2002 | Pelus et al. |
| 6,511,958 B1 | 1/2003 | Atkinson et al. |
| 2005/0163760 A1* | 7/2005 | Cartier-Lacave et al. . 424/93.21 |

FOREIGN PATENT DOCUMENTS

| | | | |
|---|---|---|---|
| EP | 0264166 | | 4/1988 |
| WO | WO-03/047635 | | 6/2003 |
| WO | WO03/047635 | * | 6/2003 |

OTHER PUBLICATIONS

Peled et al. (Science. 1999; 283: 845-848).*
Sawada et al (J. Exp. Med., May 4, 1998; 187(9): 1439-1449).*
Abkowitz et al., Mobilization of hematopoietic stem cells during homeostasis and after cytokine exposure, Blood, 102:1249-1253, 2003.
Aiuti et al., Correction of ADA-SCID by stem cell gene therapy combined with nonmyeloblative conditioning, Science, 296:2410-2413, 2002.
Alison, Cell differentiation: hepatocytes from non-hepatic adult stem cells, Nature, 406:257, 2000.
Anfinsen, Principles that govern the folding of protein chains, Science, 181:223-230, 1973.
Azizi, Engraftment and migration of human bone marrow stromal cells implanted in the brains of albino rats—similarities to astrocyte grafts, Proc. Natl. Acad. Sci. (USA), 95:3908-3913, 1998.
Banerji et al., A lymphocyte-specific cellular enhancer is located downstream of the joining region in immunoglobulin heavy chain genes, Cell, 33:729-740, 1983.
Barquinero et al., Efficient transduction of human hematopoietic repopulating cells generating stable engraftment of transgene-expressing cells in NOD/SCID mice, Blood, 95:3085-3093, 2000.
Bhatia et al., Purification of primitive human hematopoietic cells capable of repopulating immune-deficient mice, Proc. Natl. Acad. Sci. (USA), 94:5320-5325, 1997.
Bjornson et al., Turning brain into blood: a hematopoietic fate adopted by adult neural stem cells in vivo, Science, 283:534-537, 1999.
Bleul et al., A highly efficacious lymphocyte chemoattractant, stromal cell-derived factor 1 (SDF-1), J. Exp. Med., 184:1101-1109, 1996.
Bongso et al., Improved quality of human embryos when co-cultured with human ampullary cells, Hum. Reprod., 4:706-713, 1989.
Brelot et al., Identification of residues of CXCR4 critical for human immunodeficiency virus coreceptor and chemokine receptor activities, J. Biol. Chem., 275:23736-23744, 2000.

(Continued)

*Primary Examiner* — Scott Long
(74) *Attorney, Agent, or Firm* — Marshall, Gerstein & Borun LLP

(57) ABSTRACT

The present invention relates to stem cells suitable for transplantation and to methods for their preparation.

26 Claims, 8 Drawing Sheets

OTHER PUBLICATIONS

Broxmeyer et al., Enhanced myelopoiesis in sdf-I-transgenic mice: sdf-1 modulates myelopoeisis by regulating progenitor cell survival and inhibitory effects of myelosuppresive chemokines [abstract 2886], Blood, 94:650a, 1999.

Broxmeyer et al., Stromal cell-derived factor-1/CXCL12 directly enhances survival/antiapoptosis of myeloid progenitor cells through CXCR4 and Gαi proteins and enhances engraftment of competitive, repopulating stem cells, J. Leukoc. Biol., 73:630-638, 2003.

Byrne et al., Multiplex gene regulation: a two-tiered approach to transgene regulation in transgenic mice, Proc. Natl. Acad. Sci. (USA), 86:5473-5477, 1989.

Calame et al., Transcriptional controlling elements in the immunoglobulin and T cell receptor loci, Adv. Immunol., 43:235-275, 1988.

Cartron et al., Quantitive and qualitative analysis of the human primitive progenitor cell compartment after autologous stem cell transplantation, J. Hematother. Stem Cell Res., 11:359-368, 2002.

Cashman et al., Changes in the proliferative activity of human hematopoietic stem cells in NOD/SCID mice and enhancement of their transplantibility after in vivo treatment with cell cycle inhibitors, J. Exp. Med., 196:1141-1149, 2002.

Cashman et al., Stromal-derived factor 1 inhibits the cycling of very primitive human hematopoietic cells in vitro and in NOD/SCID mice, Blood, 99:792-799, 2002.

Cavazzana-Calvo et al., Gene therapy of human severe combined immunodeficiency (SCID)-X1 disease, Science, 288:669-672, 2000.

Chan et al., Adhesion receptors on haematopoietic progenitor cells, Br. J. Haematol., 112:541-557, 2001.

Denning-Kendall et al., Cytokine expansion culture of cord blood $CD34^+$ cells induces marked and sustained changes in adhesion receptor and CXCR4 expressions, Stem Cells, 21:61-70, 2003.

Edlund et al., Cell-specific expression of the rat insulin gene: evidence for role of two distinct 5' flanking elements, Science, 230:912-916, 1985.

Eglitis et al., Hematopoietic cells differentiate into both microglia and macroglia in the brains of adult mice, Proc. Natl. Acad. Sci. (USA), 94:4080-4085, 1997.

Forbes et al., Adult stem cell plasticity: new pathways of tissue regeneration become visible, Clin. Sci. (London), 103:355-369, 2002.

Förster et al., Intracellular and surface expression of the HIV-1 coreceptor CXCR4/fusin on various leukocyte subsets: rapid internalization and recycling upon activation, J. Immunol., 160:1522-1531, 1998.

Gao et al., Repopulation of liver endothelium by bone-marrow-derived cells, Lancet, 357:932-933, 2001.

Gardner et al., Culture and transfer of human blastocysts increases implantation rates and reduces the need for multiple embryo transfers, Fertil. Steril., 69:84, 1998.

Gibellini et al., Stroma-derived factor Iα induces a selective inhibition of human erythroid development via the functional upregulation of Fas/CD95 ligand, Br. J. Haematol., 111:432-440, 2000.

Grafte-Faure et al., Recruitment of primitive peripheral blood cells: synergism of interleukin 12 with interleukin 6 and stromal cell-derived Factor-1, Cytokine, 12:1-7, 2000.

Grantham, Amino acid difference formula to help explain protein evolution, Science, 185:862-864, 1974.

Guenechea et al., Transduction of human $CD34^+CD38^-$ bone marrow and cord blood-derived SCID-repopulating cells with third generation lentiviral vectors, Mol. Ther., 1:566-573, 2000.

Hall et al., Decreased homing of retrovirally transduced human bone marrow $CD34^+$ cells in the NOD/SCID mouse model, Exp. Hematol., 34:433-442, 2006.

Hao et al., Extended long-term culture reveals a highly quiescent and primitive human hematopoietic progenitor population, Blood, 88:3306-3313, 1996.

Hattori et al., Plasma elevation of stromal-derived factor-1 induces mobilization of mature and immature hematopoietic progenitor and stem cells, Blood, 97:3354-3360, 2001.

International Preliminary Report on Patentability, PCT/IL2004/001018, European Patent Office, completed Nov. 21, 2005.

International Search Report, PCT/IL2004/001018, European Patent Office, completed Apr. 15, 2005.

Jackson et al., Regeneration of ischemic cardiac muscle and vascular endothelium by adult stem cells, J. Clin. Invest., 107:1395-1402, 2001.

Jankowska-Wieczorek et al., Autocrine/paracrine mechanisms in human hematopoiesis, Stem Cells, 19:99-107, 2001.

Kahn et al., Overexpression of CXCR4 on human $CD34^+$ progenitors increases their proliferation, migration, and NOD/SCID repopulation, Blood, 103:2942-2949, 2004.

Kang et al., Persistent low-level engraftment of rhesus peripheral blood progenitor cells transduced with the fanconi anemia C gene after conditioning with low-dose irradiation, Mol Ther., 3:911-919, 2001.

Kawabata et al., A cell-autonomous requirement for CXCR4 in long-term lymphoid and myeloid reconstitution, Proc. Natl. Acad. Sci. (USA), 96:5663-5667, 1999.

Kollet et al., HGF, SDF-1, and MMP-9 are involved in stress-induced human $CD34^+$ stem cell recruitment to the liver, J. Clin. Invest., 112:160-169, 2003.

Kollet et al., Human $CD34^+CXCR4^-$ sorted cells harbor intracellular CXCR4, which can be functionally expressedand provide NOD/SCID repopulation, Blood, 100:2778-2786, 2002.

Kollet et al., Rapid and efficient homing of human $CD34^+CD38^{-/low}$ $CXCR4^+$ stem and progenitor cells to the bone marrow and spleen of NOD/SCID and NOD/SCID/B2m$^{null}$ mice, Blood, 97:3283-3291, 2001.

Krause et al., Multi-organ, multi-lineage engraftment by a single bone marrow-derived stem cell, Cell, 105:369-377, 2001.

Lagaaij, Endothelial cell chimerism after renal transplantation and vascular rejection, Lancet, 357:33-37, 2001.

Lagasse, Purified hematopoietic stem cell can differentiate into hepatocytes in vivo, Nat. Med., 6:1229-1234, 2000.

Lapidot et al., The essential roles of the chemokine SDF-1 and its receptor CXCR4 in human stem cell homing and repopulation of transplanted immune-deficient NOD/SCID and NOD/SCID/B2m$^{null}$ mice, Leukemia, 16:1992-2003, 2002.

Lataillade et al., Chemokine SDF-1 enhances circulating $CD34^+$ cell proliferation in synergy with cytokines: possible role in progenitor survival, Blood, 95:756-768, 2000.

Lataillade et al., Stromal cell-derived factor 1 regulates primitive hematopoiesis by suppressing apoptosis and by promoting $G_0/G_1$ transition in $CD34^+$ cells: evidence for an autocrine/paracrine mechanism, Blood, 99:1117-1129, 2002.

Levesque et al., SDF-Ia is inactivated by proteolytic cleavage in the bone marrow of mice mobilized by either G-CSF or cyclophosphamide, Blood, 98:831a, 2001.

Louache et al., Expression of CD4 by human hematopoietic progenitors, Blood, 84:3344-3355, 1984.

Ma et al., Impaired B-lymphopoiesis, myelopoiesis, and derailed cerebellar neuron migration in $CXCR4^-$ and SDF-1-deficient mice, Proc. Natl. Acad. Sci. (USA), 95:9448-9453, 1998.

Ma e al., The chemokine receptor CXCR4 is required for the retention of B lineage and granulocytic precursors within the bone marrow microenvironment, Immunity, 10:463-471, 1999.

Mezey et al., Turning blood into brain: cells bearing neuronal antigens generated in vivo from bone marrow, Science, 290:1779-1782, 2000.

Miyoshi et al., Transduction of human $CD34^+$ cells that mediate long-term engraftment of NOD/SCID mice by HIV vectors, Science, 283:682-686, 1999.

Moore et al., Mobilization of endothelial and hematopoietic stem and progenitor cells by adenovector-mediated elevation of serum levels of SDF-1, VEGF, and angiopoietin-1, Ann. NY Acad. Sci., 938:36-45, 45-37, 2001.

Morrison et al., The biology of hematopoietic stem cells, Annu. Rev. Cell. Dev. Biol., 11:35-71, 1995.

Nagasawa et al., Defects of B-cell lymphopoiesis and bone-marrow myelopoiesis in mice lacking the CXC chemokine PBSF/SDF-1, Nature, 382:635-638, 1996.

Naldini et al., In vivo gene delivery and stable transduction of nondividing cells by a lentiviral vector, Science, 272:263-267, 1996.

Orlic et al., Bone marrow cells regenerate infarcted myocardium, Nature, 410:701-705, 2001.

Papayannopoulou, Bone marrow homing: the players, the playfield, and their evolving roles, Curr. Opin. Hematol., 10:214-219, 2003.

Peled et al., Dependence of human stem cell engraftment and repopulation of NOD/SCID mice on CXCR4, Science, 283:845-848, 1999.

Petersen et al., Bone marrow as a potential source of hepatic oval cells, Science, 284: 1168-1170, 1999.

Petit et al., G-CSF induces stem cell mobilization by decreasing bone marrow SDF-1 and up-regulating CXCR4, Nat. Immunol., 3:687-694, 2002.

Pinkert et al., An albumin enhancer located 10 kb upstream functions along with its promoter to direct efficient, liver-specific expression in transgenic mice, Genes Dev., 1:268-277, 987.

Podesta et al., Deficient reconstitution of early progenitors after allogeneic bone marrow transplantation, Bone Marrow Trans., 19:1011-1017, 1997.

Podesta, Transplantation hematopoiesis, Curr. Opin. Hematol., 8:331-336, 200.

Ponomaryov et al., Induction of the chemokine stromal-derived factor-1 following DNA damage improves human stem cell function, J. Clin. Invest., 106:1331-1339, 2000.

Poulsom et al., Bone marrow contributes to renal parenchymal turnover and regeneration, J. Pathol., 195:229-235, 2001.

Rusten et al., TNF-a and TGF-13 potently upregulate the expression of CXCR4 on peripheral blood progenitor cells, Blood, 94:252a, 2000.

Sawada et al., Disturbed $CD4^+$ T cell homeostasis and in vitro HIV-1 susceptibility in transgenic mice expressing T cell line-tropic HIV-1 receptors, J. Exp. Med., 187:1439-1449, 1998.

Selleri et al., Long-lasting decrease of marrow and circulating long-term culture initiating cells after allogeneic bone marrow transplant, Bone Marrow Trans., 23:1029-1037, 1999.

Shamblott et al., Derivation of pluripotent stem cells from cultured human primordial germ cells, Proc. Natl. Acad. Sci. (USA), 95:13726-13731, 1998.

Shen et al., CXCR-4 desensitization is associated with tissue localization of hemopoietic progenitor cells, J. Immunol., 166:5027-5033, 2001.

Shen et al., Molecular basis of transdifferentiation of pancreas to liver, Nat. Cell Biol., 2:879-887, 2000.

Signoret et al., Phorbol esters and SDF-1 induce rapid endocytosis and down modulation of the chemokine receptor CXCR4, J. Cell Biol., 139:651-664, 1997.

Spencer et al., Enumeration of bone marrow 'homing' haemopoietic stem cells from G-CSF-mobilised normal donors and influence on engraftment following allogeneic transplantation, Bone Marrow Trans., 28:1019-1022, 2001.

Sutton et al.. Transduction of human progenitor hematopoietic stem cells by human immunodeficiency virus type 1-based vectors is cell cycle dependent, J. Virol., 73:3649-3660, 1999.

Sweeney et al., Sulfated polysaccharides increase plasma levels of SDF-1 in monkeys and mice: involvement in mobilization of stem/progenitor cells, Blood, 99:44-51, 2002.

Thiese et al., Liver from bone marrow in humans, Hepatology, 32:11-16, 2000.

Thomson et al., Primate embryonic stem cells, Curr. Topics Dev. Biol., 38:133-165, 1998.

Thomson et al., Isolation of a primate embryonic stem cell line, Proc. Natl. Acad. Sci. (USA), 92: 7844-7848, 1995.

Thomson et al., Embryonic stem cell lines derived from human blastocysts, Science, 282: 1145-1147, 1998.

Tomita et al., Autologous transplantation of bone marrow cells improves damaged heart function, Circulation, 100:II247-II256, 1999.

Voermans et al., In vitro migratory capacity of $CD34^+$ cells is related to hematopoietic recovery after autologous stem cell transplantation, Blood, 97:799-804, 2001.

Wagstaff et al., Gene transfer using a disabled herpes virus vector containing the EMCV IRES allows multiple gene expression in vitro and in vivo, Gene Ther., 5:1566-1570, 1998.

Wang et al., SCID-repopulating cell activity of human cord blood-derived $CD34^-$ cells assured by intra-bone marrow injection, Blood, 101:2924-2931, 2003.

Wang et al., Liver repopulation and correction of metabolic liver disease by transplanted adult mouse pancreatic cells, Am. J. Pathol., 158:571-579, 2001.

Weissman, Stem cells: units of development, units of regeneration, and units in evolution, Cell, 100:157-168, 2000.

Whetton et al., Homing and mobilization in the stem cell niche, Trends Cell Biol., 9: 233-238, 1999.

Williams et al., Host repopulation of the endothelium in allografts of kidneys and aorta, Surg. Forum, 20:293-294, 1969.

Winoto et al., A novel, inducible and T cell-specific enhancer located at the 3' end of the T cell receptor alpha locus, EMBO J., 8:729-733, 1989.

Woodbury et al., Adult rat and human bone marrow stromal cells differentiate into neurons, J. Neurosci. Res., 61:364-370, 2000.

Woods et al., Lentiviral gene transfer into primary and secondary NOD/SCID repopulating cells, Blood, 96:3725-3733, 2000.

Wright et al., Hematopoietic stem cells are uniquely selective in their migratory response to chemokines, J. Exp. Med., 195:1145-1154, 2002.

Wright et al., Physiological migration of hematopoietic stem and progenitor cells, Science, 294:1933-1936, 2001.

Written Opinion of the International Searching Authority, PCT/IL2004/001018, European Patent Office, completed Apr. 15, 2005.

Yahata et al., A highly sensitive strategy for SCID-repopulating cell assay by direct injection of primitive human hematopoietic cells into NOD/SCID mice bone marrow, Blood, 101:2905-2913, 2003.

Zufferey et al., Multiply attenuated lentiviral vector achieves efficient gene delivery in vivo, Nat. Biotechnol., 15:871-875, 1997.

* cited by examiner

STEM CELLS SUITABLE FOR TRANSPLANTATION, THEIR PREPARATION AND PHARMACEUTICAL COMPOSITIONS COMPRISING THEM

This application is a continuation of U.S. patent application Ser. No. 10/578,291, filed Feb. 5, 2007, which is the U.S. National Stage of International Application No. PCT/IL04/01018, filed Nov. 8, 2004, which claims the priority benefit of Israeli Patent Application No. 158868, filed Nov. 13, 2003.

FIELD OF THE INVENTION

The present invention relates to stem cells suitable for transplantation and to methods for their preparation.

BACKGROUND OF THE INVENTION

Clinical and experimental hematopoietic stem cells (HSC) transplantation procedures mimic the physiological process of HSC migration from the circulation into the bone marrow (BM) occurring during late embryonic development and steady state hematopoiesis in adults throughout life[1-3]. Gene transfer into human HSC may serve as a promising tool in the correction of a wide variety of hematopoietic and genetic disorders. HSC transplantation can be used to durably deliver these genetically modified cells to the BM, which in turn will release mature cells with the corrected gene into the circulation throughout life.

Enhanced efficacy of stem cell engraftment could improve the outcome of clinical transplantations as well as gene therapy protocols, and might be achieved by modulating the ability of stem cells to home to and repopulate the recipient BM. For this purpose, a better understanding of the mechanisms, which regulate these processes, is necessary.

Interactions between the chemokine stromal-derived factor-1 (SDF-1) also referred to as CXCL12, and its receptor CXCR4 play an essential role in stem cell seeding of the BM during murine embryonic development[10,11]. Previously, the present inventors were able to show, using immune deficient NOD/SCID mice as recipients, that both the short term in vivo migration (homing) and high-level multilineage repopulation of the murine bone marrow by human CD34$^+$ enriched cells are dependent on SDF-1/CXCR4 interactions[12-15]. In support of these data, it has been shown that either high levels of CXCR4 expression on human CD34$^+$ cells, or high SDF-1 induced directional motility in vitro, correlates with faster recovery in both allogeneic and autologous clinical transplantations with positive selection of CD34$^+$ cells[16,17].

CXCR4 expression is a dynamic process, which is regulated by environmental factors such as cytokines, chemokines, stromal cells, adhesion molecules, and proteolytic enzymes[18]. In hematopoietic stem and progenitor cells of human origin, CXCR4 can be upregulated from intracellular pools by short term (~40 hr) in vitro cytokine culture[13,19] or stimulation of cord blood (CB) CD34$^+$ with proteolytic enzymes such as MMP-2 and MMP-9[20]. This subsequently enhances their in vitro to migration towards an SDF-1 gradient[13] as well as their in vivo homing and repopulation capacities in transplanted NOD/SCID and serially transplanted β2mnull NOD/SOD mice[12,13], linking stem cell self renewal and development with motility. A recent report demonstrated that longer culture periods with a cytokine cocktail results in a decrease in cell surface CXCR4 expression on human CB CD34$^+$ enriched cells[22] and reduced repopulation was documented with human progenitors cultured in vitro for longer periods[23]. Recently, the present inventors showed that CB CD34$^+$/CXCR4$-$ sorted cells harbor low levels of intracellular CXCR4, which, following short term in vitro cytokine stimulation, can rapidly be functionally expressed on the cell surface to mediate SDF-1 dependent homing and repopulation of transplanted NOD/SCID mice[15].

In addition to their central role in mediating directional migration of human and murine stem cells[24], SDF-1/CXCR4 interactions are also involved in other stem cell functions. Of importance, SDF-1/CXCR4 interactions are also involved in retention of stem and progenitor cells in the BM[10,32,33]. This hypothesis has also been confirmed by other studies which demonstrated the involvement of SDF-1/CXCR4 interactions in the anchorage of human HSC injected directly into the murine BM cavity[34,35]. Interference of these interactions induces release/mobilization of both human and murine progenitors from the BM into the circulation[36-41].

Transgenic mice overexpressing human CD4 and CXCR4 on their CD4$^+$ T cells have increased levels of these cells in their BM and only very low levels in the circulation[42]. Therefore, overexpression of CXCR4 on human CD34$^+$ progenitor cells may facilitate their homing and repopulation potential.

Lentiviral vectors have been used to introduce transgenes into SCID repopulating cells (SRCs)[43-46], due to their unique ability to transduce non-dividing cells[47]. Furthermore, a significant clinical breakthrough in gene therapy was made in patients with human severe combined immunodeficiency (SCID)-X1 resulting in full correction of disease phenotype[48,49], proving that gene therapy can work in practice. However, emerging evidence exists for impaired homing[8] and low engraftment[9] of retrovirally-transduced human CD34$^+$ cells.

It is well documented that low concentrations of SDF-1 in synergy with other early to acting cytokines enhance proliferation of both human CD34$^+$ cells and murine stem and progenitor cells, suggesting a role for this chemokine in progenitor cell survival[25-29], while high levels of SDF-1 induce quiescence of proliferating human long term culture initiating cells (LTCIC) and primitive human fetal liver CD34$^+$ stem cells capable of serial repopulation of transplanted NOD/SCID mice[30,31].

One of the disadvantages of BM transplantation is the long lasting reduced levels of immature progenitors, such as long-term culture initiating cells (LTCIC), (1 log reduction) in the BM of transplanted patients compared to healthy individuals[4-7].

Long-term culture-initiating cells (LTC-IC) are hematopoietic progenitors able to generate colony-forming unit-cells (CFU) after 5 to 8 weeks (35 to 60 days) of culture on bone marrow (BM) stroma and represent progenitors currently detectable in vitro. It has been reported that long-term cultures initiated with CD34+CD38− cells from human BM or cord blood are able to continue generating CFU for at least 100 days, i.e., beyond the standard LTC-IC period. Single-cell cultures from cord blood were used to study whether the subpopulation of CD34+CD38− cells is able to generate CFU beyond 60 days ("extended long-term culture-initiating cells" or ELTC-IC). In contrast, to LTC-IC cord blood, ELTC-IC proliferate later in culture and are a more quiescent progenitor population. ELTC-IC generates threefold to fourfold more progeny than did LTC-IC (P<0.002). This is a functional hierarchy of progenitors in long-term culture, which correlates with their level of quiescence. (Blood. 1996 Nov. 1; 88(9): 3306-13 Crooks G M et al.

In view of the ever-expanding use of stem cell therapy, it is highly desirable to enhance the levels of CD34+CD38− cell in the population of stem cells to improve the efficiency and success rate of cell replacement therapy.

SUMMARY OF THE INVENTION

The invention relates to a method for preparing a population of cells comprising stem cells with a high amount of immature primitive progenitors, the method comprising collecting stem cells and introducing into the cells a DNA fragment comprising the sequence of CXCR4.

In one embodiment of the invention, the population of cells exhibits improved CXCR4 signaling in response to low concentration of SDF-1.

In another embodiment of the invention, the population of cells exhibits improved CXCR4 signaling in response to high concentration of SDF-1.

In a further embodiment of the invention, the stem cells are hematopoietic stem cells, preferably, CD34+ enriched.

In a further embodiment of the invention, the immature primitive progenitors are of the CD34+/CD38−/low lineage.

In a further embodiment of the invention, the collection of the stem cells is effected after a stem cell mobilization procedure; and/or after a surgical procedure.

In a further embodiment of the invention, after collection, stem cells having CXCR4 levels above a predetermined threshold are isolated e.g. by FACS.

In a further embodiment of the invention, the stem cells of the invention are capable of differentiating towards the myeloid and erythroid lineages.

In a further embodiment of the invention, the amount of the immature primitive progenitors of the CD34+/CD38−/low lineage are about 1-5% of the population.

In a further embodiment of the invention, the amount of immature primitive progenitors of the CD34+/CD38−/low lineage are equal to or higher than about 3% of the stem cells.

In a further embodiment of the invention, the low concentration of SDF-1 is equal to or lower than about 50 ng/ml.

In a further embodiment of the invention, improved signaling is manifested by enhancement of cell migration mediated by low concentrations of SDF-1.

In a another further embodiment of the invention, improved signaling is manifested by enhancement of cell proliferation mediated by low concentrations of SDF-1.

In a further embodiment of the invention, the high concentration of SDF-1 is equal to or higher than about 1 microgram/ml.

In a further embodiment of the invention, improved signaling is manifested by a reduction in desensitization by SDF-1.

In one aspect, the invention provides a population of cells comprising stem cells comprising a high amount of immature primitive progenitors, and exhibiting improved CXCR4 signaling capability in response to low and/or high concentrations of SDF-1, prepared by introducing to the stem cells a DNA fragment comprising the CXCR4 sequence.

In one embodiment of the invention, the stem cells are hematopoietic stem cells.

In a further embodiment of the invention, the population of cells is capable of differentiating towards the myeloid and erythroid lineages.

In a further embodiment of the invention, the hematopoietic stem cells are CD34+ enriched stem cells.

In a further embodiment of the invention, the immature primitive progenitors are of the CD34+/CD38−/low lineage.

In a further embodiment of the invention, the amount of CD34+/CD38−/low is about 1-5% of the population.

In a another further embodiment of the invention, the amount of CD34+/CD38−/low is about and above 3% of the population.

In a further embodiment of the invention, the low concentration of SDF-1 is about and below 50 ng/ml.

In a further embodiment of the invention, the high concentration of SDF-1 is equal to or higher than about 1 microgram/ml.

In another aspect, the invention provides the use of the population of cells of the invention in the manufacture of a medicament for increasing homing of stem cells to a target tissue in a subject in need.

Also, the invention provides the use of the population of cells of the invention in the manufacture of a medicament for increasing repopulation of cells to a target tissue in a subject in need.

In one embodiment of the invention, the target tissue is selected from the group consisting of bone marrow, blood vessel, heart, lung, liver, pancreas, kidney, nervous system, skin, bone and skeletal muscle.

In one embodiment of the invention, the population of cells of the invention is used to facilitate transplantation.

In a further embodiment of the invention, transplantation follows chemotherapy protocols.

In another further embodiment of the invention, transplantation is autologous.

In another further embodiment of the invention, the transplantation involves mobilisation of autologous cells.

In another further embodiment of the invention, transplantation is heterologous.

In another further embodiment of the invention, transplantation is carried out with mobilized stem cells.

In addition, the invention provides a method of treating a disorder in a subject, requiring cell or tissue replacement, the method comprising providing to a subject in need thereof a therapeutically effective amount of the population of cells according to the invention.

Also, the invention provides a method for preparing a population of cells comprising stem cells exhibiting CXCR4 with intact 6H8 epitope, the method comprises collecting stem cells and introducing to the stem cells a DNA fragment comprising the sequence of CXCR4.

In another aspect, the invention provides a population of cells comprising stem cells comprising intact CXCR4 6H8 epitope prepared by introducing to the stem cells a DNA fragment comprising the sequence of CXCR4, and use of the population of cells in the manufacture of a medicament for transplantation in a subject in need.

An additional aspect of the invention relates to a method for treating a disorder requiring cell or tissue replacement, the method comprises providing to a subject in need thereof a therapeutically effective amount of a population of cells according to the invention.

Also, the invention provides a pharmaceutical composition comprising a population of cells comprising stem cells exhibiting intact CXCR4 6H8 epitope prepared by introducing to stem cells a DNA fragment comprising the sequence of CXCR4.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
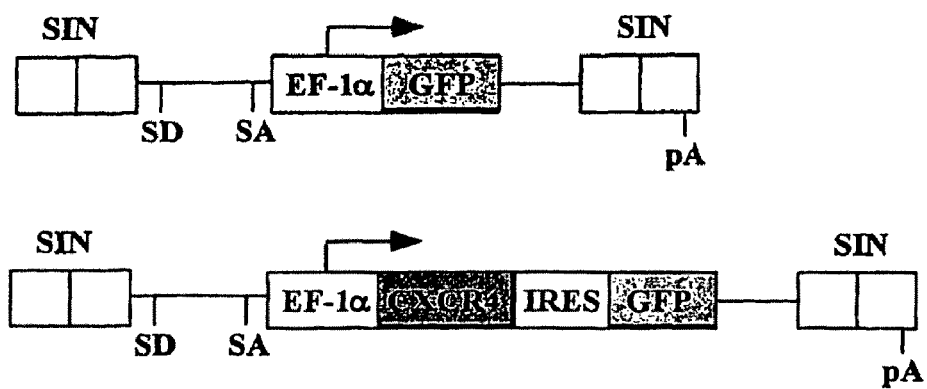
FIG. 1 shows a schematic representation of the lentiviral vector constructs. Only the relevant portions of the integrated provirus are depicted. The EF1-α promoter is used to drive expression of either green fluorescent protein (GFP) cDNA in the control vector (upper panel) or the CXCR4-IRES-GFP bicistronic cassette of the experimental vector (lower panel). SD=splice donor, SA=splice acceptor, pA=polyadenylation signal, SIN=self-inactivating vector.

The present invention relates to stem cells enriched with immature primitive progenitors, and having improved CXCR4 signaling in response to low and high concentration of SDF-1, and to methods of generating and using the same. More specifically, the cells of the invention are capable of responding to low concentrations of SDF-1 and are less desensitized by high concentrations of SDF-1. Specifically, the present invention allows treatment of disorders requiring cell or tissue replacement. The present invention is based on results demonstrating that transgenic stem cells overexpressing CXCR4 exhibit enhanced levels of CD34+/CD38−/low cell population and/or exhibit improved CXCR4 signaling capability in response to low and high concentration of SDF-1 and exhibit intact CXCR4 6H8 epitope.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The use of cellular therapy is growing rapidly, and is gradually becoming an important therapeutic modality in treatment of various disorders. Hematopoietic stem cell (HSC) (e.g., from the bone marrow, umbilical cord blood or mobilized peripheral blood) transplantation is one example of a routinely practiced, insurance-reimbursed cellular therapy. However, many other cellular therapies are being developed as well, including immunotherapy for cancer and infectious diseases, chondrocyte therapy for cartilage defects, neuronal cell therapy for neurodegenerative diseases, and stem cell therapy for numerous applications [Forbes (2002) Clinical Science 103:355-369].

One of the problems associated with stem cell therapy is the difficulty of achieving long-term successful engraftment of cells at the target tissue. Currently, patients who were successfully transplanted exhibit very low levels of stem cells and immature progenitors, which generate cells with the desired phenotype.

Treatment of CD34$^+$ progenitor cells with cytokines such as HGF and MMPs has been previously shown to upregulate expression of CXCR4 and exhibit better response to SDF-1. However, under increasing concentrations of SDF-1, CXCR4 is internalized and the cells are less responsive to SDF-1. Also, increasing the levels of SDF-1 induces desensitization and quiescence of proliferating human long term culture initiating cells (LTCIC) and primitive human fetal liver CD34$^+$ stem cells capable of serial repopulation of transplanted NOD/SCID mice[30,31].

One of the problems of BM transplantation is the reduced levels of long lasting immature progenitors (1 log reduction) in the BM of transplanted patients compared to healthy individuals[4-7].

The present inventors have found that transgenic hematopoietic stem cells overexpressing CXCR4 show unexpected high levels of the CD34+/CD38−/low cell population.

The results obtained demonstrate that transgenic stem cells, such as CB and MBP CD34+ enriched cells, are successfully transduced with lentiviral vectors expressing high levels of the CXCR4 transgene. For example in one embodiment transduced cells are 87±2.7% (CB) and 80±4% (MPB) positive for cell surface CXCR4 expression whereas only 28±3.1% of both CB and MPB CD34$^+$ cells infected with the GFP vector expressed endogenous CXCR4.

Figure 3:
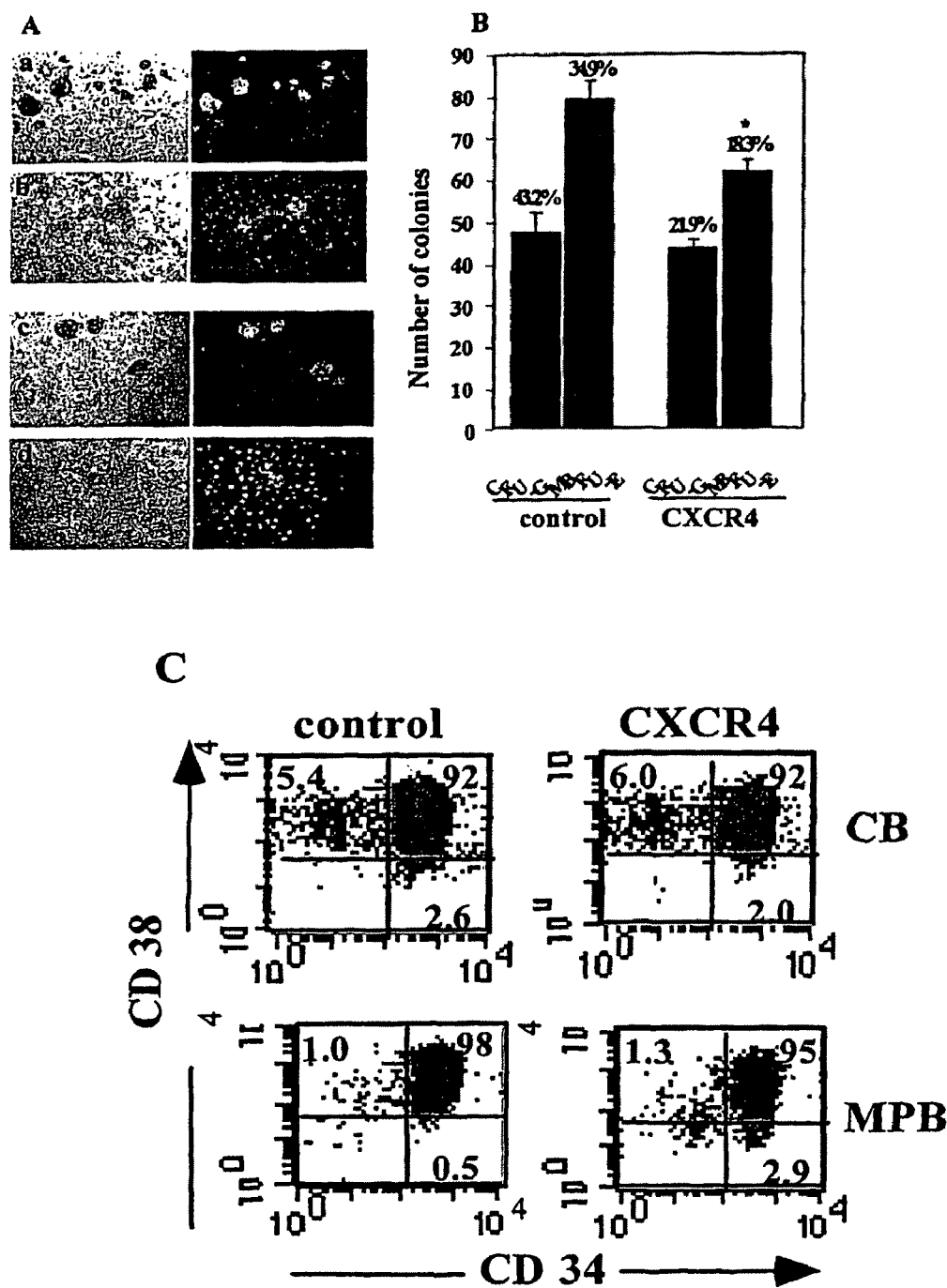
FIG. 3 shows clonogenic progenitor content of transduced CB CD34+ cells. Lentiviral transduced CB CD34$^+$ cells were seeded in semisolid methylcellulose culture. A. GFP$^+$ colony forming cell (CFC) colonies were analyzed by phase contrast microscopy at day 14. Upper panel indicates BFU-E (a) and CFU-GM (b) colonies from control vector transduced cells. Lower panel indicates BFU-E (c) and CFU-GM (d) from CXCR4 transduced cells. A representative experiment is shown. B. Data indicate total number of CFU-GM and BFU-E colonies. Numbers above bars indicate percentage of GFP$^+$ colonies out of total colonies. Bars represent mean±SE of three independent experiments. *p=0.004 compared to BFU-E colonies of GFP-transduced cells. C. CB and MPB CD34+ cells were labeled with human anti-CD34 and anti-CD38 mAbs. Numbers indicate percent positive cells from entire population. A representative experiment out of 3 is shown.

It is shown that transgenic cells overexpressing CXCR4 are not affected in their ability to differentiate towards the myeloid and erythroid lineages. In accordance with the the invention, it is demonstrated that transduced CD34$^+$ cells (both control and CXCR4) showed multilineage differentiation into GFP CFC colonies such as burst-forming unit-erythroid (BFU-E) and colony-forming unit-granulocyte, macrophage (CFU-GM), scored by phase contrast microscopy at day 14 (FIG. 3A).

Unexpectedly, MPB CD34+ CXCR4 transduced cells demonstrated a higher percentage (2.9%) of CD34+/CD38−/low population compared to 0.5% in control cells. This effect was not observed in CB CD34+ cells (FIG. 3C). CXCR4 transduction therefore support grow and/or preservation of the CD34+/CD38−/low primitive population.

Also, unexpectedly, CXCR4 transduced stem cells show more intact CXCR4 6H8 epitope in the surface of the stem cells.

Figure 4:
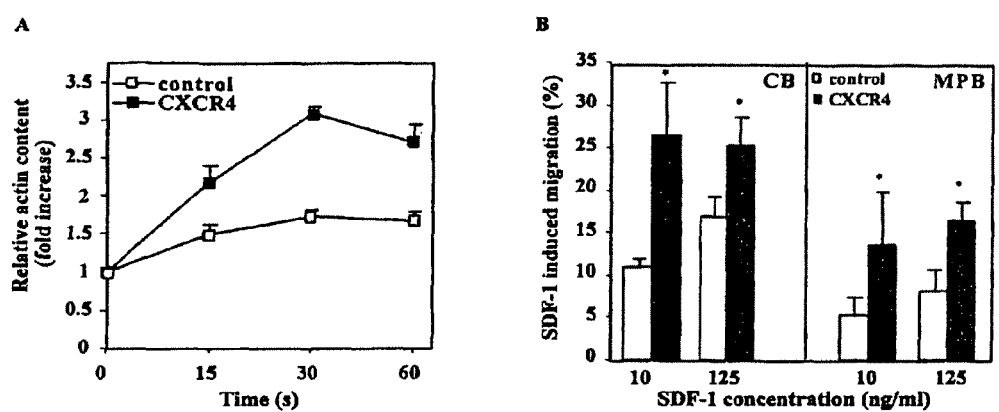
FIG. 4 shows functionality of CXCR4 expressed on transduced CD34+ cells. A. CXCR4-transduced CB CD34$^+$ cells were stimulated with SDF-1 (300 ng/ml) for the indicated times and intracellular F-actin content was measured by FACS. Data indicates fold increase in F-actin content following stimulation with SDF-1 compared to unstimulated cells. Data represent mean±SE of three independent experiments. B. CXCR4-transduced CB and MPB CD34+ cells were tested in a transwell migration assay for their migration towards different SDF-1 concentrations as indicated. Data indicate percent migrating cells to SDF-1. Bars represent mean±SE of five independent experiments. *p<0.04 (CB), *p=0.03 (MPB) compared to control GFP-transduced cells at 125 ng/ml SDF-1. *p<0.05 (CB), *p<0.05 (MPB) compared to control GFP-transduced cells at 10 ng/ml SDF-1.

Transgenic cells overexpressing CXCR4 exhibit significantly increased response to SDF-1 mediated chemotaxis of 1.5±0.04 (p<0.001) fold for CB and 2.3±0.3 (p=0.03) fold for MPB when compared to control vector-transduced cells (FIG. 4B). In addition transgenic cells overexpressing CXCR4 show increased actin polymerization and/or increased cell motility mediated by SDF-1. It was found in accordance with the invention, that CD34$^+$ cells overexpressing CXCR4 show a 3±0.11 (p<0.001) fold increase in actin polymerization versus a 1.5±0.07 (p=0.002) fold increase in control cells when compared to unstimulated cells (FIG. 4A).

Thus, overexpression of CXCR4 on human progenitor cells results in enhanced SDF-1 induced signaling, leading to an increase in cell motility and actin polymerization.

Furthermore, on assessment of proliferation of CXCR4 overexpressing cells over a seven day period, it was observed that CXCR4-transduced CB CD34+ cells had almost doubled their seeded number, while control cell number, had decreased to below the original amount seeded.

Figure 6:
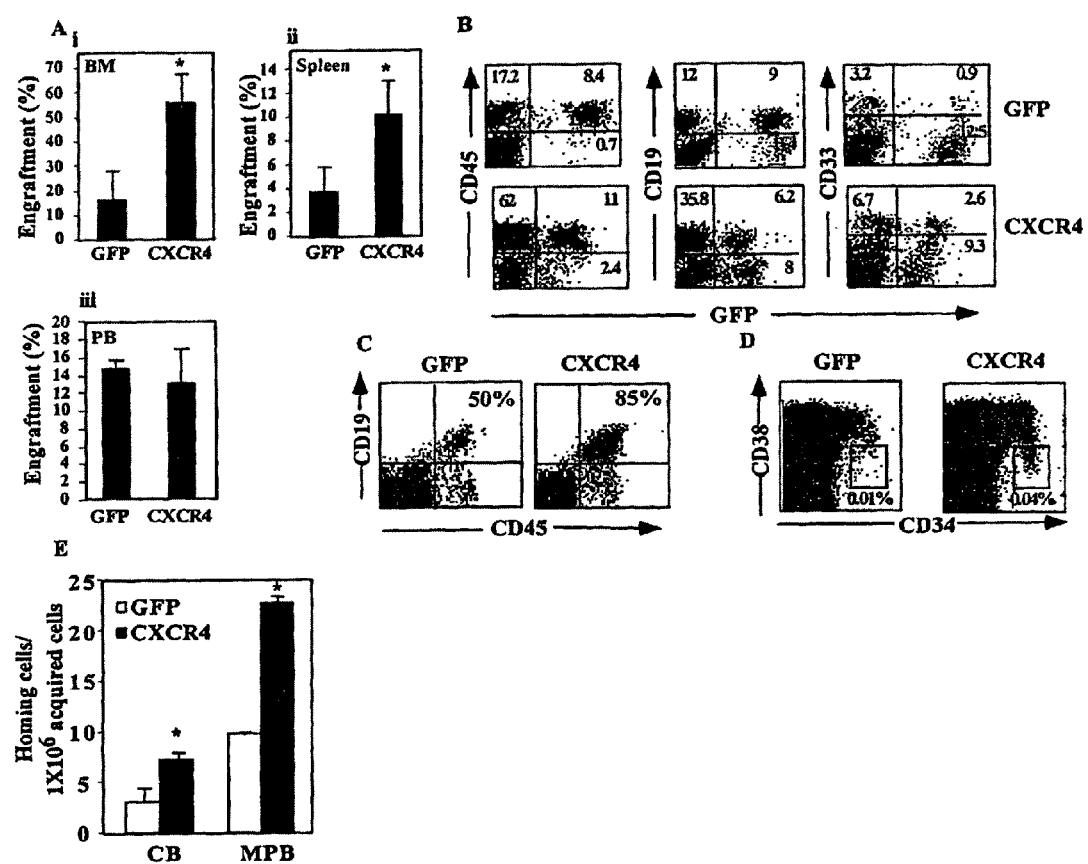
FIG. 6 shows in vivo multilineage reconstitution and GFP expression of CXCR4 overexpressing SCID repopulating cells (SRC). CXCR4-transduced CB CD34+ cells were injected into sublethally irradiated NOD/SCID mice. Five weeks post transplantation mice were examined for the presence of human repopulating cells when compared to control GFP-transduced cells. A. Murine BM (i), spleen (ii) and peripheral blood (PB) (iii) were analyzed for human cell engraftment by FACS analysis detecting % of human CD45+ cells. Bars represent mean±SE of nine independent experiments performed in duplicate or triplicate. *p<0.005 compared to control GFP-transduced cells. B. Lymphoid and myeloid differentiation of human SRC in a representative NOD/SCID transplant recipient is shown by CD19 and CD33 antibody staining respectively. Numbers indicate percent of positive cells out of total live population. C. BM cells were stained for the human specific pan leukocyte marker CD45 and the B cell lineage differentiation marker CD19 and analyzed by FACS. Numbers indicate percentage of CD19 cells calculated from total CD45 population. Data show a representative experiment. D. Engrafted murine BM cells were stained with human specific anti-CD34 and anti-CD38 mAbs and analyzed by flow cytometry. Numbers indicate percentage of primitive, undifferentiated CD34+/38−/low cells. Data show a representative experiment. E. Homing of enriched, immature CD34+ cells to the spleen was determined 16 h (MPB) or 2 h (CB) post transplantation by staining with human specific anti-CD34 and anti-CD38 mAbs. Bars represent mean±SE of 3 independent experiments performed in duplicate. *p<0.05 compared to control cells.

CXCR4-transduced cells demonstrated increased engraftment of up to 4±0.7 (p=0.001) fold for CB CD34$^+$ cells when compared to control cells (FIG. 6A). Furthermore, a representative FACS staining with CD19 and CD33 monoclonal antibodies demonstrates that multilineage hematopoiesis into lymphoid and myeloid populations respectively was maintained in transduced cells (FIG. 6B) with a trend to more B-cell lymphopoiesis in mice transplanted with CXCR4-transduced cells (FIG. 6C), most probably since SDF-1 is also a Pre B cell growth factor. Furthermore, an average of 36%±19% (range 7.5% to 77%) of the CD45$^+$ cells were found to express GFP (FIG. 6B). Transgene expression was also detected in both myeloid and lymphoid populations (FIG. 6B). Mice transplanted with CXCR4 overexpressing cells showed a four fold increase in the primitive CD34$^+$/CD38$^{-/low}$ cell population in the BM compared to mice injected with control vector-transduced cells (FIG. 6D), suggesting that the higher engraftment levels of CXCR4-overexpressing cells are due to increased repopulation of the more primitive cell population.

It was observed that two hours (CB) or 16 h (MPB) post transplantation CXCR4-transduced cells showed a more than two fold increase in homing to the spleen compared to their control counterparts (FIG. 6E). However these differences were not detected in their homing capacity to the BM (data not shown). These results suggest that CXCR4-transduced cells may first home short term to the spleen before repopulating (5 weeks post transplantation) the BM as previously suggested (Papayannopoulou T. *Curr Opin Hematol.* 2003; 10:214-219, Ref 18: Kollet O, *Blood.* 2001; 97:3283-3291).

The present findings enable the generation of stem cells, which can be efficiently recruited to a target tissue and repopulate it, and as such can be used in numerous clinical applications, such as in repair of liver injury and in liver or bone marrow transplantation.

Thus, according to one aspect of the present invention there is provided a method to get "extended long-term culture-initiating cells" or ELTC-IC or of increasing the primitive CD34$^+$/CD38$^{-/low}$ cell population. According to another aspect of the present invention there is provided a method to get ELTC-IC cells capable to respond to SDF-1 even when exposed to increased SDF-1 concentrations.

As used herein, the phrase "stem cells" refers to cells, which are capable of differentiating into other cell types having a particular, specialized function (i.e., "fully differentiated" cells).

As used herein a "transgenic cell" is a cell carrying an introduced gene or segment.

Non-limiting examples of stem cells, which can be used according to this aspect of the present invention, are hematopoietic stem cells (HSCs) and mesenchymal stem cells (MSCs) obtained from bone marrow tissue of an individual at any age or from cord blood of a newborn individual, embryonic stem (ES) cells obtained from the embryonic tissue formed after gestation (e.g., blastocyst), or embryonic germ (EG) cells obtained from the genital tissue of a fetus any time during gestation, preferably before 10 weeks of gestation. Further description of stem cells, which can be used according to this aspect of the present invention, is summarized herein below.

HSCs—Hematopoietic stem cells (HSCs) are the formative pluripotential blast cells found inter alia in fetal liver, umbilical cord blood, bone marrow and peripheral blood which are capable of differentiating into any of the specific types of hematopoietic or blood cells, such as erythrocytes, lymphocytes, macrophages and megakaryocytes. Typically, within the bone marrow, HSCs reside in niches that support all the requisite factors and adhesive properties to maintain their ability and produce an appropriate balanced output of mature progeny over the life time of the organism [Whetton (1999) Trends Cell Biol 9:233-238; Weissman (2000) Cell 100:157-168; Jankowska-Wieczorek (2001) Stem Cells 19:99-107; Chan (2001) Br. J. Haematol. 112:541-557].

HSCs according to this aspect of the present invention are preferably CD34+ cells and more preferably CD34+/CD38−/low cells, which are a more primitive stem cell population and are therefore less lineage-restricted, and were shown to be the major long-term BM repopulating cells.

MSCs—Mesenchymal stem cells are the formative pluripotential blast cells found inter alia in bone marrow, blood, dermis and periosteum that are capable of differentiating into more than one specific type of mesenchymal or connective tissue (i.e. the tissues of the body that support the specialized elements; e.g. adipose, osseous, stroma, cartilaginous, elastic and fibrous connective tissues) depending upon various influences from bioactive factors, such as cytokines.

Approximately, 30% of human marrow aspirate cells adhering to plastic are considered as MSCs. These cells can be expanded in vitro and then induced to differentiate. The fact that adult MSCs can be expanded in vitro and stimulated to form bone, cartilage, tendon, muscle or fat cells render them attractive for tissue engineering and gene therapy strategies. In vivo assays have been developed to assay MSC function. MSCs injected into the circulation can integrate into a number of tissues described hereinabove. Specifically, skeletal and cardiac muscle can be induced by exposure to 5-azacytidine and neuronal differentiation of rat and human MSCs in culture can be induced by exposure to β-mercaptoethanol, DMSO or butylated hydroxyanisole [Tomita (1999) 100: 11247-11256; Woodbury (2000) J. Neurosci. Res. 61:364-370]. Furthermore, MSC-derived cells are seen to integrate deep into brain after peripheral injection as well as after direct injection of human MSCs into rat brain; they migrate along pathways used during migration of neural stem cells developmentally, become distributed widely and start lose markers of HSC specialization [Azizi (1998) Proc. Natl. Acad. Sci. USA 95:3908-3913]. Methods for promoting mesenchymal stem and lineage-specific cell proliferation are disclosed in U.S. Pat. No. 6,248,587.

Epitopes on the surface of the human mesenchymal stem cells (hMSCs) such as SH2, SH3 and SH4 described in U.S. Pat. No. 5,486,359 can be used as reagents to screen and capture mesenchymal stem cell population from a heterogeneous cell population, such as exists, for example, in bone marrow. Precursor mesenchymal stem cells, which are positive for CD45, are preferably used according to this aspect of the present invention, since these precursor mesenchymal stem cells can differentiate into the various mesenchymal lineages.

Preferred stem cells according to this aspect of the present invention are human stem cells.

Table 1, below provides examples of adult stem cells, which can be used to obtain the indicated phenotype in a target tissue of interest, according to this aspect of the present invention.

TABLE 1

| Stem cell | Differentiated phenotype | Target tissue | Reference |
| --- | --- | --- | --- |
| Bone marrow | Oval cells, Hepatocytes | Liver | Petersen (1999) Science 284: 1168-1170 |
| KTLS cells | Hepatocytes | Liver | Lagasse (2000) Nat. Med. 6: 1229-1234 |
| Bone marrow | Hepatocytes | Liver | Alison (2000) Nature 406: 257; Thiese (2000) Hepatology 32: 11-16 |
| Pacreatic exocrine cells | Hepatocytes | Liver | Shen (2000) Nat. Cell Biol. 2: 879-887 |
| Pacreas | Hepatocytes | Liver | Wang (2001) Am. J. Pathol. 158: 571-579 |
| Bone marrow | Endothelium | Liver | Gao (2001) Lancet 357: 932-933 |
| Bone marrow | Tubular epithelium, glomeruli | Kidney | Poulsom (2001) J. Pathol. 195: 229-235 |
| Bone marrow | Endothelium | Kidney | Lagaaij (2001) Lancet 357: 33-37 |
| Extra renal | Endothelium | Kidney | Williams (1969) Surg. Forum 20: 293-294 |
| Bone marrow | Myocardium | Heart | Orlic (2001) Nature 410: 701-704 |
| Bone marrow | Cardiomyocytes and Endothelium | Heart | Jackson (2001) J. Clin Invest. 107: 1395-1402 |
| Bone marrow | Type 1 pneumocytes | Lung | Krause (2001) Cell 105: 369-377 |
| Neuronal | Multiple | Marrow | Bjornson (1999) Science 283: 534-537 |

TABLE 1-continued

| Stem cell | Differentiated phenotype | Target tissue | Reference |
|---|---|---|---|
| | hematopoietic lineages | | |
| Bone marrow | Neurons | CNS | Mezey (2000) Science 290: 1779-1782 |
| Bone marrow | Microglia and Astrocyes | CNS | Eglitis (1997) Proc. Natl. Acad. Sci. USA 94: 4080-4085 |

Abbreviations: SP—Side population cells; CNS—central nervous system;

As mentioned hereinabove the stem cells according to this aspect of the present invention are successfully transduced with lentiviral vectors with high expression of the CXCR4 transgene.

The terms "polypeptide and protein" in the present specification are interchangeable.

The present invention also concerns muteins of the above CXCR4 protein of the invention, which muteins retain essentially the same biological activity of the CXCR4 protein having essentially only the naturally occurring sequences of the CXCR4. Such "muteins" may be ones in which up to about 20, preferably no more than 10 amino acid residues may be deleted, added or substituted by others in the CXCR4 protein respectively, such that modifications of this kind do not substantially change the biological activity of the protein mutein with respect to the protein itself.

These muteins are prepared by known synthesis and/or by site-directed mutagenesis techniques, or any other known technique suitable thereof.

Any such mutein preferably has a sequence of amino acids sufficiently duplicative of that of the basic the CXCR4 such as to have substantially similar activity thereto. Thus, it can be determined whether any given mutein has substantially the same activity as the basic protein of the invention by means of routine experimentation comprising subjecting such a mutein to the biological activity tests set forth in Examples below.

Muteins of the CXCR4 protein which can be used in accordance with the present invention, or nucleic acid coding thereof, include a finite set of substantially the CXCR4 corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., Principles of Protein Structure, Springer-Verlag, New York, 1978; and Creighton, T. E., Proteins: Structure and Molecular Properties, W.H. Freeman & Co., San Francisco, 1983, which are hereby incorporated by reference. For a presentation of nucleotide sequence substitutions, such as codon preferences, see. See Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

Preferred changes for muteins in accordance with the present invention are what are known as "conservative" substitutions. Conservative amino acid substitutions of those in the protein having essentially the naturally-occurring CXCR4 sequences, may include synonymous amino acids within a group, which have sufficiently similar physicochemical properties that substitution between members of the group will preserve the biological function of the molecule, see Grantham, Science, Vol. 185, pp. 862-864 (1974). It is clear that insertions and deletions of amino acids may also be made in the above-defined sequence without altering its function, particularly if the insertions or deletions only involve a few amino acids, e.g., under 50, and preferably under 20 CXCR4 and do not remove or displace amino acids which are critical to a functional conformation, e.g., cysteine residues, Anfinsen, "Principles That Govern The Folding of Protein Chains", Science, Vol. 181, pp. 223-230 (1973). Muteins produced by such deletions and/or insertions come within the purview of the present invention. Preferably, the synonymous amino acid groups are those defined in Table A. More preferably, the synonymous amino acid groups are those defined in Table B; and most preferably the synonymous amino acid groups are those defined in Table C.

TABLE A

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE B

More Preferred Groups of
Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE C

Most Preferred Groups of
Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of the protein for use in the present invention include any known method steps, such as presented in U.S. Pat. Nos. RE 33,653, U.S. Pat Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Straw et al).

In another preferred embodiment of the present invention, any mutein of the CXCR4 protein for use in the present invention has an amino acid sequence essentially corresponding to that of the above noted CXCR4 protein of the invention. The term "essentially corresponding to" is intended to comprehend muteins with minor changes to the sequence of the basic protein which do not affect the basic characteristics thereof, particularly insofar as its ability to the CXCR4 is concerned. The type of changes which are generally considered to fall within the "essentially corresponding to" language are those which would result from conventional mutagenesis techniques of the DNA encoding the CXCR4 protein of the invention, resulting in a few minor modifications, and screening for the desired activity for example increasing the sensitivity of stem cells to a chemoattractant.

The present invention also encompasses CXCR4 variants. A preferred CXCR4 variant are the ones having at least 80% amino acid identity, a more preferred the CXCR4 variant is one having at least 90% identity and a most preferred variant is one having at least 95% identity to CXCR4 amino acid sequence.

The term "sequence identity" as used herein means that the amino acid sequences are compared by alignment according to Hanks and Quinn (1991) with a refinement of low homology regions using the Clustal-X program, which is the Windows interface for the ClustalW multiple sequence alignment program (Thompson et al., 1994). The Clustal-X program is available over the internet at ftp://ftp-igbmc.u-strasbg.fr/pub/clustalx/. Of course, it should be understood that if this link becomes inactive, those of ordinary skill in the art could find versions of this program at other links using standard internet search techniques without undue experimentation. Unless otherwise specified, the most recent version of any program referred herein, as of the effective filing date of the present application, is the one, which is used in order to practice the present invention.

Another method for determining "sequence identity" is the following. The sequences are aligned using Version 9 of the Genetic Computing Group's GDAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Muteins in accordance with the present invention include those encoded by a nucleic acid, such as DNA or RNA, which hybridizes to DNA or RNA under stringent conditions and which encodes a the CXCR4 protein in accordance with the present invention, comprising essentially all of the naturally-occurring sequences encoding the CXCR4 and sequences which may differ in its nucleotide sequence from the naturally-derived nucleotide sequence by virtue of the degeneracy of the genetic code, i.e., a somewhat different nucleic acid sequence may still code for the same amino acid sequence, due to this degeneracy.

The term "hybridization" as used herein shall include any process by which a strand of nucleic acid joins with complementary strand through a base pairing (Coombs J, 1994, Dictionary of Biotechnology, stokton Press, New York N.Y.). "Amplification" is defined as the production of additional copies of a nucleic acid sequence and is generally carried out using polymerase chain reaction technologies well known in the art (Dieffenbach and Dveksler, 1995, PCR Primer, a Laboratory Manual, Cold Spring Harbor Press, Plainview N.Y.).

"Stringency" typically occurs in a range from about Tm-5° C. (5° C. below the melting temperature of the probe) to about 20° C. to 25° C. below Tm.

The term "stringent conditions" refers to hybridization and subsequent washing conditions, which those of ordinary skill in the art conventionally refer to as "stringent". See Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

As used herein, stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA-DNA hybrid:

$$Tm=81.5 C+16.6 (\log M)+0.41 (\% GC)-0.61 (\% \text{form})-500/L$$

where M is the molarity of monovalent cations, % GC is the percentage of G and C nucleotides in the DNA, % form is the percentage of formamide in the hybridization solution, and L is the length of the hybrid in base pairs. For each 1 C that the Tm is reduced from that calculated for a 100% identity hybrid, the amount of mismatch permitted is increased by about 1%. Thus, if the Tm used for any given hybridization experiment at the specified salt and formamide concentrations is 10 C below the Tm calculated for a 100% hybrid according to the equation of Meinkoth, hybridization will occur even if there is up to about 10% mismatch.

As used herein, "highly stringent conditions" are those which provide a Tm which is not more than 10 C below the Tm that would exist for a perfect duplex with the target sequence, either as calculated by the above formula or as actually measured. "Moderately stringent conditions" are those, which provide a Tm, which is not more than 20 C below the Tm that would exist for a perfect duplex with the target sequence, either as calculated by the above formula or as actually measured. Without limitation, examples of highly stringent (5-10 C below the calculated or measured Tm of the hybrid) and moderately stringent (15-20 C below the calculated or measured Tm of the hybrid) conditions use a wash solution of 2×SSC (standard saline citrate) and 0.5% SDS (sodium dodecyl sulfate) at the appropriate temperature below the calculated Tm of the hybrid. The ultimate stringency of the conditions is primarily due to the washing conditions, particularly if the hybridization conditions used are those, which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6× SSPE (standard saline-phosphate-EDTA), 5× Denhardt's reagent, 0.5% SDS, 100 µ g/ml denatured, fragmented salmon sperm DNA at a temperature approximately 20 to 25 C below the Tm. If mixed probes are used, it is preferable to use tetramethyl ammonium chloride (TMAC) instead of SSC (Ausubel, 1987, 1999). Adult stem cells can be obtained using a surgical procedure such as bone marrow aspiration or can be harvested using commercial systems such as those available from Nexell Therapeutics Inc. Irvine, Calif., USA. Stem cells utilized by the present invention are preferably collected (i.e., harvested) using a stem cell mobilization procedure, which utilizes chemotherapy or cytokine stimulation to release of HSCs into circulation of subjects. Stem cells are preferably retrieved using this procedure since mobilization is known to yield more HSCs and progenitor cells than bone marrow surgery.

Stem cell mobilization can be induced by a number of molecules. Examples include but are not limited to cytokines such as, granulocyte colony-stimulating factor (G-CSF), granulocyte-macrophage colony-stimulating factor (GM-CSF), interleukin (IL)-7, IL-3, IL-12, stem cell factor (SCF), and flt-3 ligand; chemokines like IL-8, Mip-1α, Groβ, or SDF-1; and the chemotherapeutic agents cyclophosphamide (Cy) and paclitaxel. It will be appreciated that these molecules differ in kinetics and efficacy, however, according to presently known embodiments G-CSF is preferably used alone or in combination such as with cyclophosphamide to mobilize the stem cells. Typically, G-CSF is administered daily at a dose of 5-10 µg/kg for 5-10 days. Methods of mobilizing stem cells are disclosed in U.S. Pat. Nos. 6,447,766 and 6,162,427. Human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium, which enables its outgrowth. Following 9 to 15 days, the ICM derived outgrowth is dissociated into clumps either by a mechanical dissociation or by enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 1-2 weeks.

For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; Gardner et al., [Fertil. Steril. 69: 84, 1998].

It will be appreciated that commercially available stem cells can be also be used according to this aspect of the present invention. Human ES cells can be purchased from the NIH human embryonic stem cells registry (<http://escr.nih.gov>). Non-limiting examples of commercially available embryonic stem cell lines are BG01, BG02, BG03, BG04, CY12, CY30, CY92, CY10, TE03, and TE32.

Human EG cells can be retrieved from the primordial germ cells obtained from human fetuses of about 8-11 weeks of gestation using laboratory techniques known to anyone skilled in the arts. The genital ridges are dissociated and cut into small chunks, which are thereafter disaggregated into cells by mechanical dissociation. The EG cells are then grown in tissue culture flasks with the appropriate medium. The cells are cultured with daily replacement of medium until cell morphology consistent with EG cells is observed, typically after 7-30 days or 1-4 passages. For additional details on methods of preparing EG cells see Shamblott et al., [Proc. Natl. Acad. Sci. USA 95: 13726, 1998] and U.S. Pat. No. 6,090,622.

It will be appreciated that enrichment of stem cell population exhibiting pluripotency may be preferably effected. Thus, for example, as outlined hereinabove, CD34+ stem cells can be concentrated using affinity cobirrins or FACS as further described hereinunder.

Culturing of stem cells under proliferative conditions may also be effected in cases where stem cell numbers are too low for use in treatment. Culturing of stem cells is described in U.S. Pat. Nos. 6,511,958, 6,436,704, 6,280,718, 6,258,597, 6,184,035, 6,132708 and 5,837,5739.

Once stem cells are obtained, they are transfected with DNA comprising the sequence encoding CXCR4 or an active portion thereof.

The "transformed, transfected or transgenic" cells are cultured under suitable conditions, which allow the expression of the protein encoded by the polynucleotide or DNA.

The stem cells can be transformed with a recombinant bacteriophage DNA, plasmid DNA or cosmid DNA expression vector comprising the CXCR4 coding sequence; lentiviruses systems are preferably used to express the CXCR4 or the active portion thereof. In any case, transformed cells are cultured under effective conditions, which allow for the expression of CXCR4. Effective culture conditions include, but are not limited to, effective media, bioreactor, temperature, pH and oxygen conditions that permit protein production. An effective medium refers to any medium in which a cell is cultured to produce the recombinant modified polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

In such cases, the expression construct includes a cis-acting regulatory element active in mammalin cells (examples above), which may be inducible, growth specific or tissue specific conditions.

Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct of the present invention can further include an enhancer, which can be adjacent or distant to the promoter sequence and can function in up regulating the transcription therefrom.

Preferably, the inducible cis-acting regulatory element is regulatable by changes in the environment of the stem cells during the homing-implantation process.

The nucleic acid construct of the present invention can further include an IRES element, preferably EMCV IRES, which can be in between the CXCR4 gene and a marker or selection gene sequence and can function in up regulating the translation of the marker or selection gene.

Once CXCR4 or active portion thereof is overexpressed, stem cells exhibiting increased response to SDF-1.

Identification and isolation of such cells overexpressing CXCR4 according to this aspect of the present invention can be effected using a number of cytological, biochemical and molecular methods, which are well known in the art.

Analysis of receptor level can be effected by flow cytometry. This approach employs instrumentation that scans single cells flowing past excitation sources in a liquid medium. The technology can provide rapid, quantitative, multiparameter analyses on single living (or dead) cells based on the measurement of visible and fluorescent light emission. This basic protocol focuses on: measure fluorescence intensity produced by fluorescent-labled antibodies and ligands that bind specific cell-associated molecules. To isolate cell populations using fluorescence activated cell sorter stem cells of the present invention are contacted with anti CXCR4 commercially available from R&D, 614 McKinley Place NE Minneapolis, Minn.

Other cytological or biochemical methods for quantitatively assessing the level of the chemotactic receptor expression include but are not limited to binding analysis using a labeled (e.g., radioactively labeled) chemokine, western blot analysis, cell-surface biotinylation and immunofluorescent staining. It will be appreciated that the receptor expression levels can also be determined at the mRNA level. For example, CXCR4 mRNA may be detected in cells by hybridization to a specific probe. Such probes may be cloned DNAs or fragments thereof, RNA, typically made by in-vitro transcription, or oligonucleotide probes, usually generated by solid phase synthesis. Methods for generating and using probes suitable for specific hybridization are well known and used in the art. Quantification of mRNA levels can be also effected using an amplification reaction [e.g., PCR, "PCR Protocols: A Guide To Methods And Applications", Academic Press, San Diego, Calif. (1990)], employing primers, which hybridize specifically to the mRNA of a chemotactic receptor of interest.

A variety of controls may be usefully employed to improve accuracy in mRNA detection assays. For instance, samples may be hybridized to an irrelevant probe and treated with RNAse A prior to hybridization, to assess false hybridization.

Functional assays can also be used to determine the chemotactic receptor expression. For example, a chemotaxis assay, which employs a gradient of the chemotactic agent (e.g., SDF-1) and follows stem cell migration through a membrane towards the chemotactic agent can be utilized to identify and isolate stem cells exhibiting increased chemotaxis. If the cells do not express enough levels of the chemotactic receptor (e.g., CXCR4), then the majority of the cells will remain on the membrane. However, upon increased expression of the chemoattractant receptor of the present invention, cells will migrate through the membrane and settle on the bottom of the well of the chemotaxis plate (see Example 3 of the Examples section It will be appreciated that a functional homing assay can also be utilized by the method of the present invention. Such an assay is described in Kollet (2001) Blood 97:3283-3291.

Stem cells exhibiting improved CXCR4 signaling capability in response to low or high SDF-1 concentrations and/or stem cell exhibiting enhanced levels of immature primitive progenitors, such CD34+/CD38−/low population, can be used in a wide range of clinical applications.

Thus, according to another aspect of the present invention there is provided a method of treating a disorder requiring cell or tissue replacement. The method is effected by providing to a subject in need thereof a therapeutically effective amount of transgenic stem cells overexpressing CXCR4 or an active portion thereof and thereby providing increasing levels of immature primitive progenitors such as CD34+/CD38−/low population with better response to SDF-1 even in an environment with increased concentrations of SDF-1, to thereby treat the disorder requiring the cell or tissue replacement in the subject. Disorders requiring cell or tissue replacement include but are not limited to various immunodeficiencies such as in T and/or B-lymphocytes, or immune disorders, such as rheumatoid arthritis. Such immunodeficiencies may be the result of viral infections, HTLVI, HTLVII, HTLVIII, severe exposure to radiation, cancer therapy or the result of other medical treatment; Hematological deficiencies including but not limited to leukemias, such as acute lymphoblastic leukemia (ALL), acute nonlymphoblastic leukemia (ANLL), acute myelocytic leukemia (AML) or chronic myelocytic leukemia (CML). Other such hematological deficiencies can be, but are not limited to, severe combined immunodeficiency (SCID) syndromes [such as, for example adenosine deaminase (ADA) deficiency and X-linked SCID (XSCID)], osteopetrosis, aplastic anemia, Gaucher's disease, thalassemia and other congenital or genetically-determined hematopoietic abnormalities; Other disorders requiring cell or tissue replacement include those associated with liver failure, pancretic failure, neurological disorders, those disorders requiring augmented bone formation such as osteoartbritis, osteoporosis, traumatic or pathological conditions involving any of the connective tissues, such as a bone defects, connective tissue defects, skeletal defects or cartilage defects.

Preferred individual subjects according to the present invention are mammals such as canines, felines, ovines, porcines, equines, bovines and preferably humans.

The stem cells according to this aspect of the present invention are preferably obtained from the subject to be treated. However stem cells may also be obtained from a syngeneic, allogeneic and less preferably from a xenogeneic donor.

It will be appreciated that when allogeneic or xenogeneic stem cells are used, the recipient subject and/or cells are preferably treated to prevent graft versus host and host versus graft rejections. Immunosuppression protocols are well known in the art and some are disclosed in U.S. Pat. No. 6,447,765.

It will be appreciated that the stem cells of the present invention can be genetically modified to express any therapeutic gene such as an antiviral agent against hepatitis further described in U.S. Pat. No. 5,928,638. The stem cells are transplanted into the recipient subject. This is generally effected using methods well known in the art, and usually involves injecting or introducing the treated stem cells into the subject using clinical tools well known by those skilled in the art (U.S. Pat. No. 6,447,765, 6,383,481, 6,143,292, and 6,326,198).

For example, introduction of the stem cells of the present invention can be effected locally or systematically via intravascular administration, such as intravenous or intraarterial administration, intraperitoneal administration, and the like. Cells can be injected into a 50 mol Fenwall infusion bag using sterile syringes or other sterile transfer mechanisms. The cells can then be immediately infused via IV administration over a period of time, such as 15 minutes, into a free flow IV line into the patient. In some embodiments, additional reagents such as buffers or salts may be added as well. The composition for administration must be formulated, produced and stored according to standard methods complying with proper sterility and stability.

Stem cell dosages can be determined according to the prescribed use. In general, in the case of parenteral administration, it is customary to administer from about 0.01 to about 5 million cells per kilogram of recipient body weight. The number of cells used will depend on the weight and condition of the recipient, the number of or frequency of administrations, and other variables known to those of skill in the art.

Further expansion of a CXCR4 overexpressing system may serve as an effective tool to improve the compromised homing and engraftment following gene therapy protocols[8,9]. In addition, CXCR4 overexpresion on human CD34+ cells may facilitate improved clinical CB CD34+ transplantation as well as autologous mobilized PBL CD34+ transplantation following chemotherapy treatment, which can both be limited due to low cell yield[6]. Furthermore other cell types such as mesenchymal stem cells possess the ability to migrate to various organs, however their levels of engraftment are particularly low. Thus, development of a system facilitating constitutive or transient CXCR4 expression on the cell surface together with induction of expression or administration of SDF-1 in the target organ could be beneficial for directional migration in vivo, as well as long-term repopulation and development of various cell types in the organ of interest in patients, as part of organ repair. We therefore suggest overexpression of CXCR4 as a universal system for regulating stem cell function and development, which could improve the outcome of many clinical protocols.

After administering the cells into the subject, the effect of the treatment may be evaluated, if desired, as known in the art. The treatment may be repeated as needed or required.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Voll Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

CXCR4-transduced Human CD34+ Cells have Increased Surface CXCR4 Expression

CXCR4 was overexpressed on human CB and MPB CD34+ enriched cells using a HIV-derived lentiviral gene transfer system. Transduced cells were analyzed for CXCR4 surface expression.

Materials and Experimental Procedures

Human cells—Cord blood (CB) cells and adult mobilized peripheral blood (MPB) cells were obtained after informed consent. CD34+ cell enrichment was effected using magnetic bead separation as previously described [Kollet (2001) Blood 97:3283-3291]. CXCR4 expression was determined by flow cytometry using purified anti human CXCR4 (clone 12G5, R&D, Minneapolis, Minn.) and secondary F (ab')2 fragment of goat anti mouse IgG FITC (Jackson, West Grove, Pa.).

Viral vector construction and production—The human CXCR4 gene lentiviral expression vector was constructed by isolating a 1.2 kb CXCR4 cDNA from human CB cells and linking it to the enhanced green fluorescent protein (GFP) gene via an internal ribosome entry site (IRES). The fragment containing the CXCR4-IRES-GFP was ligated with the EF-1α promoter to generate a self-inactivating (SIN) vector where the fragment containing the EF-1α-CXCR4-IRES-GFP bicistronic cassette was inserted into a pHR'-SIN vector backbone (Woods et al. Blood. 2000 Dec. 1; 96(12):3725-33.) kindly provided by Dr. Didier Trono, Geneva, Switzerland. The control vector lacks the CXCR4 gene and expresses only GFP (FIG. 1).

Replication-defective, self-inactivating HIV-derived lentiviral vector was generated by transient transfection of the 293T packaging cell line by means of FuGENE 6 transfection reagent (Roche Diagnostics, Mannheim Germany), utilizing a three-plasmid system: transfer vector pHR'-EF1α-GFP-SIN (control vector) or pHR'-EF1α-CXCR4-IRES-GFP-SIN for CD34+ cells or pHR'-CMV-GFP (control vector) or pHR'-CMV-CXCR4-IRES-GFP (experimental vector) for hMSCs, the envelope coding plasmid pMD.G and the packaging construct pCMVR8.91 (Zufferey R, *Nat. Biotechnol.* 1997; 15:871-875 Naldini L, *Science.* 1996;272:263-267). Twenty-four hours post-transfection, the viral supernatant was replaced with serum free medium supplemented with 2% BSA (Sigma, St. Louis, Mo., USA), 10 mg/ml Insulin (Biological Industries, Beit Haemek, Israel), 200 mg/ml Transferrin (Sigma), 0.1 mM 2-mercaptoethanol, 2 mM L-glutamine (Biological Industries), 100 mg/ml streptomycin (Biological Industries), and 10 mM Hepes (Biological Industries). Twenty-four hours later, viral supernatant was collected, filtered (0.45 μM Minisart filter, Sartorius AG, Germany), and used for transduction of target cells.

Transduction of CD34+ cells-Transduction of CD34+ cells was performed using a double transduction protocol in HSC[50]. CD34+ cells (up to $4 \times 10^5$ per well) were pre-stimulated with SCF (50 ng/ml) in 400 μl serum free medium for 24 hours in a 12-well plate. Viral supernatant (1.6 ml/35 mm well) supplemented with SCF (50 ng/ml), FLT-3L (50 ng/ml) both from R&D Systems (Minneapolis, Minn.), and IL-6 (50 ng/ml; Interpharm Laboratories, Ares-Serono Group, Ness Ziona, Israel) was added to the cells with a viral load as much as $2 \times 10^7$ TU/ml (first infection). Transduction was repeated 24 hours later (second infection). Infection efficiency was determined according to cell expression of CXCR4 using specific antihuman CXCR4-PE (12G5, 13D Pharmingen, San Diego, Calif.) and GFP (FL1 channel) by flow cytometric analysis (Kollet 2002 blood vol 100 page 2778) (FACSCalibur, Becton Dickinson (BD), San Jose, Calif.) 72 hours post transduction. Mock cells were cultured in the same conditions as transduced cells, without exposure to lentiviral vectors.

Figure 2:
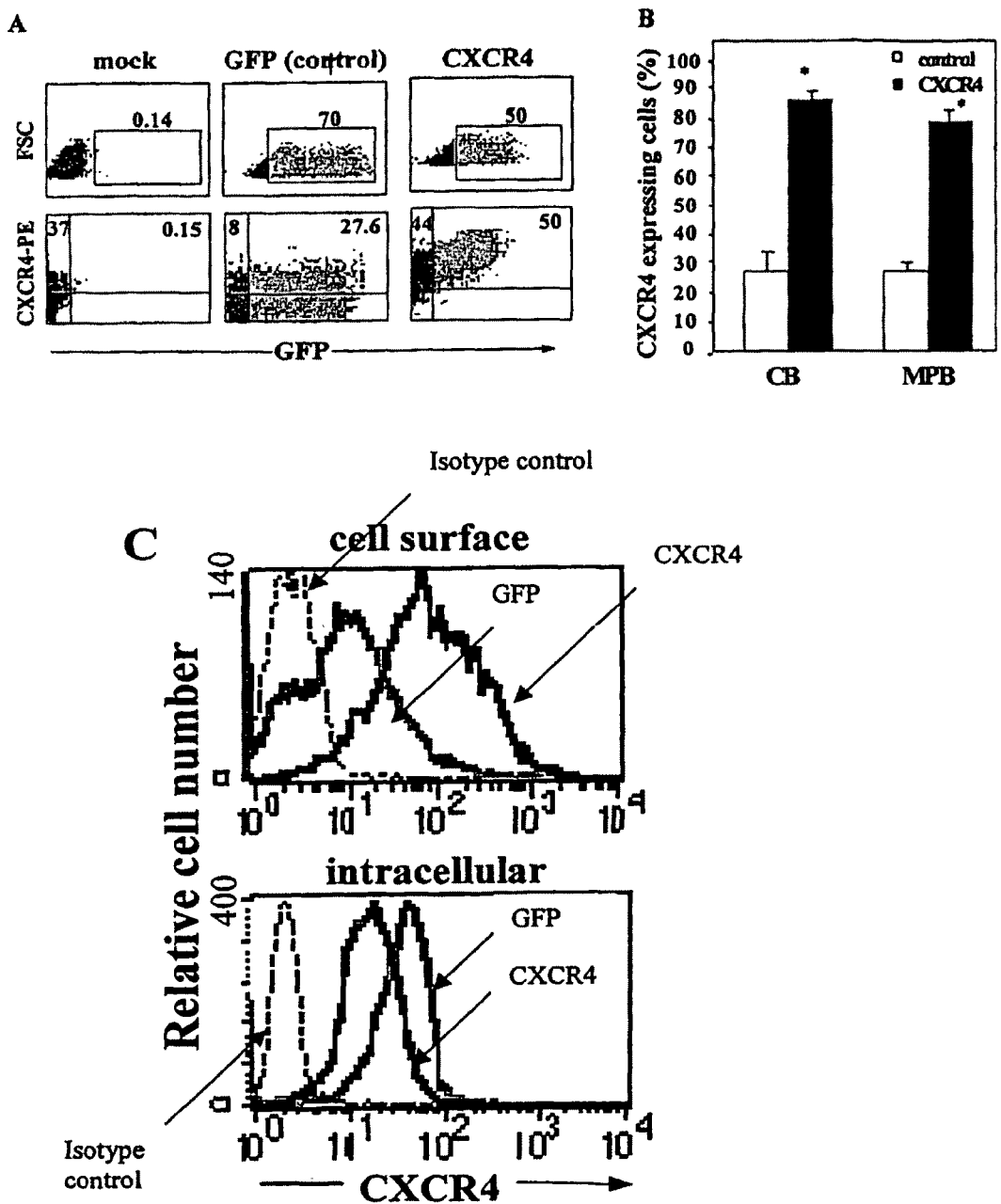
FIG. 2 shows cell surface CXCR4 expression on lentiviral-transduced human CD34+ cells. Following mock-or lentiviral infection, cord blood (CB) and mobilized peripheral blood (MPB) CD34$^+$ cells were analyzed by flow cytometry for either GFP expression alone or GFP together with CXCR4 expression using an anti-hCXCR4-PE antibody. A. Data show a representative FACS analysis from CB CD34$^+$ cells. Numbers indicate percent of total CD34$^+$ cells. Forward scattered (FSC) indicative of the cell size. B. Results indicate percentage of CB and MPB CD34$^+$ cells expressing CXCR4 and represent mean±SE of 7 independent experiments. *p<0.01 compared to control GFP-infected cells C. Immunofluorescence detection of cell surface (upper panel) and intracellular (lower panel) CXCR4 expression of GFP transduced (GFP), CXCR4 transduced (CXCR4) or isotype control cells.

It was found that both CB and MPB CD34+ cells showed high transduction efficiencies as scored by flow cytometry, reaching 70% GFP positive cells in GFP vector (control) transduced cells and 50% in CXCR4-transduced cells (FIG. 2A—upper panel). Furthermore, CXCR4-infected CD34+ cells were 87±2.7% (CB) and 80±4% (MPB) positive for cell surface CXCR4 expression whereas only 28±3.1% of both CB and MPB CD34+ cells infected with the GFP vector expressed endogenous CXCR4, resembling levels of non-transduced cells (mock cells) (FIG. 2A—lower panel (representative) and B). Interestingly, CXCR4 transduced cells showed a higher mean fluorescence intensity (MFI) of 89.4 compared to 10.2 of GFP vector transduced cells (FIG. 2C). However, their intracellular CXCR4 expression was lower than their control (GFP) counterparts (FIG. 2C). Notably, cells transduced with the CXCR4 vector had less GFP+ cells, consistent with earlier reports showing reduced expression levels of genes which are placed downstream from an IRES[51].

These results demonstrate that both CB and MPB CD34+ cells can be successfully transduced with lentiviral vectors with high expression of the CXCR4 transgene.

Example 2

CXCR4-overexpressing Human CD34+ Cells Maintain their in Vitro Differentiation Potential and Transgene Expression Stem and progenitor cells are capable in vitro of multilineage differentiation into both myeloid and erythroid lineages when provided with the appropriate cytokine cocktail (Metcalf d recent results in cancer research 1977 vol 61 page 1). We therefore assessed the effect of transgene expression on the ability of transduced cells to differentiate in vitro, in the differentiated lineages.

Experimental Procedures

CFU assay—In order to detect the levels of human progenitors as well as maintenance of transgene expression following transduction in ex vivo cultures, semisolid cultures were performed as previously described[52]. In brief, CB CD34+ transduced cells ($3 \times 10^3$ cells/ml) were plated in 0.9% methylcellulose (Sigma), 30% FCS, $5 \times 10^{-5}$M 2ME, 50 ng/ml SCF, 5 ng/ml IL-3, 5 ng/ml GM-CSF (R&D), and 2 u/ml erythropoietin (Orto Bio Tech, Don Mills, Canada). The cultures were incubated at 37° C. in a humidified atmosphere containing 5% $CO_2$ and scored 14 days later by phase contrast microscopy for GFP+ as well as myeloid or erythroid colonies by morphologic criteria.

It was found that transgene expression did not affect the ability of the cells to differentiate towards the myeloid and erythroid lineages. Transduced CD34+ cells (both control and CXCR4) showed multilineage differentiation into GFP+ CFC colonies such asburst-forming nnit-erythroid (BFU-E) and colony-forming unit-granulocyte, macrophage (CFU-GM), scored by phase contrast microscopy at day 14 (FIG. 3A). The number of GFP+ CFC colonies transduced with the control vector was 2-fold higher than GFP+ CFC colonies transduced with the CXCR4 vector, in accordance with the lower percentage of GFP+ cells following transduction with this vector (FIG. 3B). Interestingly, while both control as well as CXCR4-transduced cells produced the same number of CFU-GM colonies, there was a 25% (p=0.004) reduction in BFU-E colonies produced from CXCR4-transduced cells (FIG. 3B), confirming previous findings of Gibellini et al showing that SDF-1/CXCR4 interactions suppress erythroid lineage differentiation[53]. Furthermore, MOM CD34+ CXCR4 transduced cells demonstrated a higher percentage (2.9%) of CD34+/CD38−/low population compared to 0.5% in control cells. This effect was not observed in CB CD34+ cells (FIG. 3C). CXCR4 transduction may therefore better preserve and/or expand the CD34+/CD38−/low primitive population.

Example 3

CXCR4 Expressed on Transduced CD34+ Cells is Functional.

Chemokines induce cell motility by activating a cascade of intracellular events leading to cytoskeletal arrangements and particularly actin polymerization[54]. As a means for determining functionality of the inserted receptor, we examined the effect of CXCR4 overexpression on SDF-1 induced activation of the motility machinery.

Experimental Procedures

Actin polymerization assay—Transduced cells were stimulated with SDF-1α (300 ng/ml, Peprotech, Rocky Hill, N.J.) in serum-free RPMI at 37° C. for indicated times. Reaction was stopped by adding 3 volumes of 3.7% paraformaldehyde at RT for 10 min, followed by washing with PBS and permeabilization on ice for 2 min with 0.1% Triton-Hepes (20 mM Hepes, 300 mM sucrose, 50 mM NaCl, 3 mM MgCl2, 0.1% Triton). Cells were then stained with FITC-Phalloidin (2 mg/ml, Sigma) for 30 mit' at RT, washed and analyzed by flow cytometry.

Migration assay—RPMI (600 µl) supplemented with 10% FCS containing 125 ng/ml SDF-1α were added to the lower chamber of a Costar 24-wells transwell (Corning (pore size 5 µm), NY). $1 \times 10^5$ transduced CD34+ cells in 100 µl medium were loaded to the upper chamber and were allowed to migrate for 4 hours at 37° C. Migrating cells were collected from the lower chamber and counted for 30 seconds using a FACSCalibur. Control spontaneous migration was performed without SDF-1α in the lower chamber.

We found that CB CD34+ cells exhibited a peak of actin polymerization after 30 s stimulation with SDF-1 (FIG. 4A). At this time point, CXCR4 overexpressing cells demonstrated a 3±0.11 (p<0.001) fold increase in actin polymerization versus a 1.5±0.07 (p=0.002) fold increase in control cells when compared to unstimulated cells (FIG. 4A). In light of these results, we investigated the migration potential of CXCR4-transduced CB and MPB CD34+ cells to a gradient of SDF-1 (125 ng/ml) in a transwell migration assay. Cells overexpressing CXCR4 demonstrated a significantly increased response to SDF-1 mediated chemotaxis of 1.5±0.04 (p<0.001) fold for CB and 2.3±0.3 (p=0.03) fold for MPB when compared to control vector-transduced cells (FIG. 4B). All together, these data suggest that overexpression of CXCR4 on human enriched CD34+ progenitor cells results in enhanced SDF-1 induced signaling, leading to an increase in cell motility.

Example 4

CXCR4 Transduced CD34+ Cells are More Responsive to Low SDF-1 Concentrations

It was hypothesized that overexpression of CXCR4 on CD34+ cells may render them more responsive to low SDF-1 concentrations. In order to test this, in vitro migration of transduced cells was performed to different SDF-1 concentrations. Furthermore, low concentrations of the chemokine SDF-1 in synergy with cytokines have been shown to enhance proliferation of human CD34+ cells as well as both human and murine progenitor cell survival[25-28]. Therefore the effect of SDF-1 at low concentrations on proliferation of CXCR4 overexpressing cells was monitored.

Experimental Procedures

Migration assay—as previously described (12). Briefly, RPMI (600 µl) supplemented with 10% FCS containing either 10 ng/ml or 125 ng/ml SDF-1α were added to the lower chamber of a Costar 24-wells transwell (Corning (pore size 5 µm), NY). $1 \times 10^5$ transduced CD34+ cells in 100 µl medium were loaded to the upper chamber and were allowed to migrate for 4 hours at 37° C. Migrating cells were collected from the lower chamber and counted for 30 seconds using a FACSCalibur. Control spontaneous migration was performed without SDF-1α in the lower chamber.

Proliferation assay—Following a 96 hour transduction protocol, CB CD34+ cells were cultured for 7 days in duplicates in serum free medium supplemented with SCF 50 ng/ml, FLT-3L 50 ng/ml and IL-6 50 ng/ml in the presence or absence of SDF-1 50 ng/ml. Cells were counted daily and viability was evaluated by trypan blue exclusion.

Figure 5:
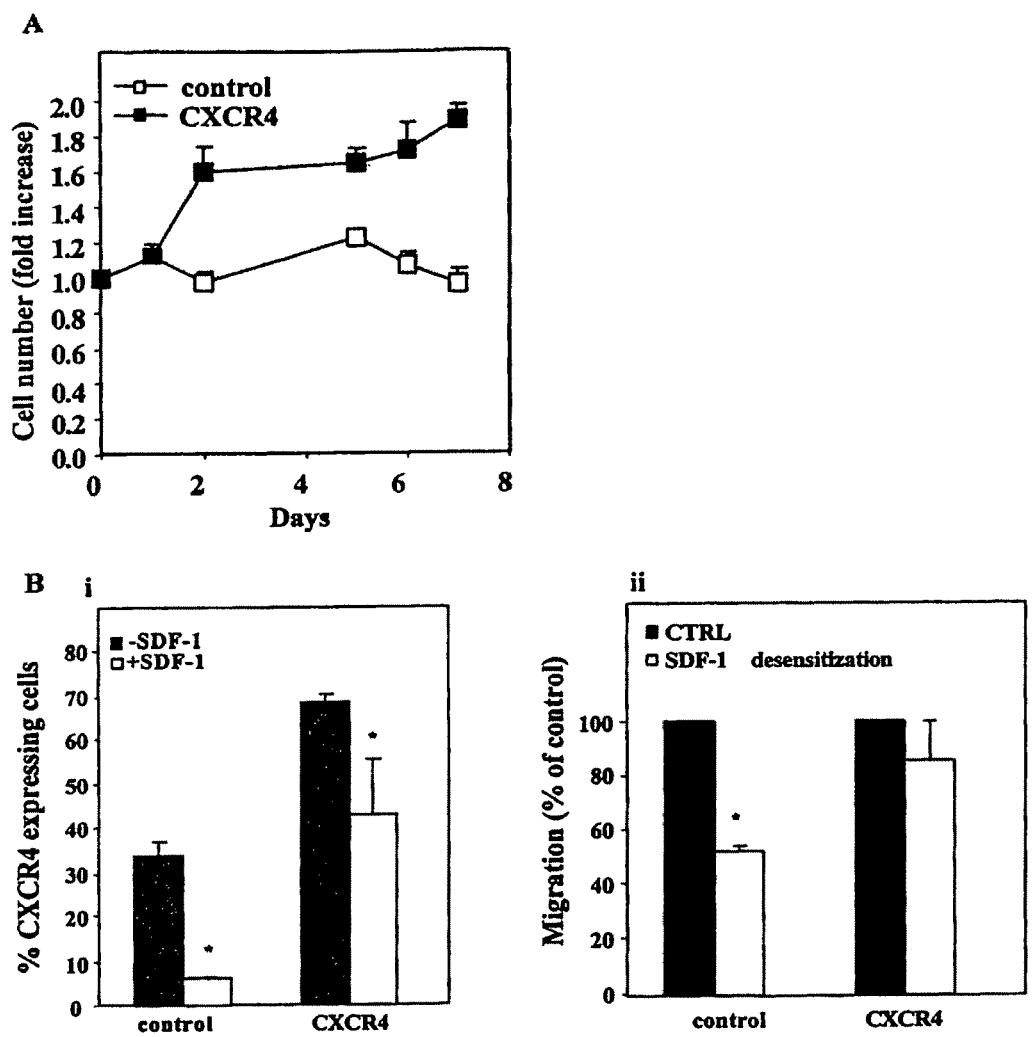
FIG. 5 shows response of CXCR4-overexpressing CB CD34+ cells to different SDF-1 concentrations. A. Lentiviral transduced CB CD34$^+$ cells were incubated for seven days in serum free conditions with SDF-1 (50 ng/ml) in combination with SCF (50 ng/ml), FLT-3L (50 ng/ml) and IL-6 (50 ng/ml). Results are shown as fold increase in number of viable cells compared to cells incubated in the absence of SDF-1. Results represent mean±SE of three independent experiments performed in duplicate. B. Lentiviral transduced CB CD34$^+$ cells were incubated overnight with 1 µg/ml SDF-1 and examined for (i) CXCR4 expression by immunostaining and (ii) SDF-1 (125 ng/ml) induced in vitro migration using a transwell migration system. Bars represent mean±SE of two independent experiments performed in duplicate. *p<0.05 compared to untreated cells (black bars).

It was found that already at low concentrations of SDF-1 (10 ng/ml), the gration of CH CXCR4-transduced cells had reached peak levels of 25%, similar to migration of these cells at a high SDF-1 concentration (125 ng/ml). As shown in FIG. 4B, at low concentrations of SDF-1 (10 ng/ml) CXCR4-infected cells isolated from human CB showed up to 2.5 fold ($p<0.05$) increase in migration compared to their control vector-transduced counterparts, while at higher SDF-1 concentrations (125 ng/ml) this increase was less significant (1.5 fold). Similarly, even though the percent of migrating cells was much lower than for CB CD34+ cells, CXCR4-transduced MPB CD34+ cells, showed a 2.6 ($p=0.05$) fold increase in migration to 10 ng/ml SDF-1 compared to a 2-fold increase to 125 ng/ml SDF-1 (FIG. 4B). Furthermore, on assessment of proliferation of CXCR4 overexpressing cells over a seven day period, it was observed that CXCR4-transduced CB $CD34^+$ cells had almost doubled their seeded amount ($p<0.05$) already 48 hours after seeding and this effect could be seen for up to seven days ($p=0.001$) in culture. Control cells, however, only increased their cell number on day five by up to only $1.2\pm0.05$ fold, and by day 7 their number had decreased to below the original amount seeded (FIG. 5A). Notably, this enhanced proliferative effect of CXCR4 overexpressing cells was not detected at higher (100 ng/ml) SDF-1 concentrations (data not shown). Longer time points in culture led to cell differentiation, ruling out the possibility of cellular transformation following lentiviral transduction. Taken together, our results indicate that overexpression of CXCR4 on $CD34^+$ cells, enhances their response to low SDF-1 concentrations, increasing both their motility and proliferation/survival, with a lesser response to high concentrations when compared to control cells.

Example 5

CXCR4 Overexpressing Cells are Less Responsive to SDF-1 Induced Desensitization.

It has been documented that SDF-1 at high concentrations (1 µg/ml and above) induces desensitization and internalization, via endocytosis, of the cell surface CXCR4 molecule, which eventually can be recycled to the cell surface[55]. We therefore tested the effect of high SDF-1 concentrations on cells overexpressing CXCR4.

Experimental Procedures

CXCR4 cell surface expression—CXCR4-transduced CB $CD34^+$ cells were incubated overnight with 1 µg/ml SDF-1. Cell surface CXCR4 expression was determined by labeling of cells with antihuman CXCR4-PE (12G5, BD Pharmingen, San Diego, Calif.) and analyzed by flow cytometry (FACSCalibur, Becton Dickinson (BD), San Jose, Calif.).

Migration assay—RPMI (600 µl) supplemented with 10% FCS containing 125 ng/ml SDF-1α were added to the lower chamber of a Costar 24-wells transwell (Corning (pore size 5 µm), NY). $1\times10^5$ transduced $CD34^+$ cells in 100 µl medium were loaded to the upper chamber and were allowed to migrate for 4 hours at 37° C. Migrating cells were collected from the lower chamber and counted for 30 seconds using a FACSCalibur. Control spontaneous migration was performed without SDF-1α in the lower chamber.

CXCR4-transduced CB $CD34^+$ cells were incubated overnight with 1 µg/ml SDF-1 and analyzed for CXCR4 cell surface expression. Unexpectedly, there was only a 40% ($p<0.05$) decrease in cell surface receptor expression in CXCR4 overexpressing cells, whereas in control cells there was up to 90% ($p<0.05$) receptor internalization (FIG. 5Bi). Following this desensitization, cells were also assayed in vitro for directional migration towards an SDF-1 (125 ng/ml) gradient. Control cells showed a significant ($p<0.05$) decrease in SDF-1 mediated migration, while the migration of CXCR4-transduced cells was hardly affected (FIG. 5Bii). This suggests that the internalization of CXCR4 is compensated for by constant overexpression of the receptor, which continuously remains functional.

Example 6

CXCR4 Overexpression Improves SRC Engraftment of NOD/SCID Mice

To assess the effect of CXCR4 overexpression on the SDF-1/CXCR4-dependent engraftment of human CB $CD34^+$ cells, transduced progenitors were transplanted in NOD/SCID mice.

Experimental Procedures

Mice. NOD/LtSz-Prkdcscid (NOD/SCID) mice were bred and maintained as previously described18. All the experiments were approved by the animal care committee of the Weizmann Institute. Eight-ten week old mice were sublethally irradiated (375 cGy, from a 60Co source) and transplanted with human cells as indicated [$2\times10^5$ cells/mouse (engraftment) and $5\times10^5$ cells/mouse (homing)] 24 hours post irradiation.

Human cell engraftment and homing—Mice were sacrificed around five weeks post transplantation and bone marrow and spleen cells were harvested and resuspended into single cell suspension. Human cell engraftment was assayed by flow cytometry (FACSCalibur, BD) using specific antihuman CD45-APC mAb (BD Pharmingen). Lineage analysis was performed by staining with anti-CD 19-PE (BD Pharmingen), or anti-CD33-PE (BD). The more primitive cell population was analysed using CD34-APC mAb (BD Pharmingen) together with anti-CD38-PE (BD). Human cells were also analysed for GFP expression (FL1 channel). Human plasma and mouse IgG were used to block Fc receptors. Isotype control antibodies and cells obtained from mice that did not undergo transplantation were used as negative controls and human CB $CD34^+$ cells were used as positive controls.

We found that CXCR4-transduced cells demonstrated increased engraftment of human cells in the murine BM of up to $4\pm0.7$ ($p=0.001$) fold for CB $CD34^+$ cells when compared to control cells (FIG. 6Ai). Similarly, CXCR4-transduced cells showed a $2.7\pm0.8$ ($p=0.05$) fold increase in repopulation of the spleen (FIG. 6Aii). Interestingly, no significant differences were observed in the numbers of circulating human cells in mice transplanted with control or CXCR4-transduced cells (FIG. 6Aiii). Furthermore, a representative FACS staining with CD19 and CD33 monoclonal antibodies demonstrates that multilineage hematopoiesis into lymphoid and myeloid populations respectively was maintained in the murine BM (FIG. 6B) with a trend to more B-cell lymphopoiesis in mice transplanted with CXCR4-transduced cells (FIG. 6C), most probably since SDF-1 is also a Pre B cell growth factor. Furthermore, an average of 36%±19% (range 7.5% to 77%) of the $CD45^+$ cells were found to express GFP (FIG. 6B). Transgene expression was also detected in both myeloid and lymphoid populations (FIG. 6B). Mice transplanted with CXCR4 overexpressing cells showed a four fold increase in the primitive $CD34^+/CD38^{-/low}$ cell population compared to mice injected with control vector-transduced cells (FIG. 6D), suggesting that the higher engraftment levels of CXCR4-overexpressing cells are due to increased repopulation of the more primitive cell population.

It has been previously demonstrated that homing of immature human CD34+38–/lowCXCR4+ cells to the murine BM and spleen is dependent on CXCR4/SDF-1 interactions[18]. Therefore it was further examined whether overexpression of CXCR4 on human CD34+ cells could improve their homing to the BM and spleen of sublethally irradiated NOD/SCID mice. It was observed that two hours (CB) or 16 h (MPB) post transplantation CXCR4-transduced cells showed a more than two fold increase in homing to the spleen compared to their control counterparts (FIG. 6E). However these differences were not detected in their homing capacity to the BM (data not shown). These results suggest that CXCR4-transduced cells may first home short term to the spleen before repopulating (5 weeks post transplantation) the BM as previously suggested[18].

Example 7

Antigenic Determinants on Overexpressed CXCR4

Figure 7:
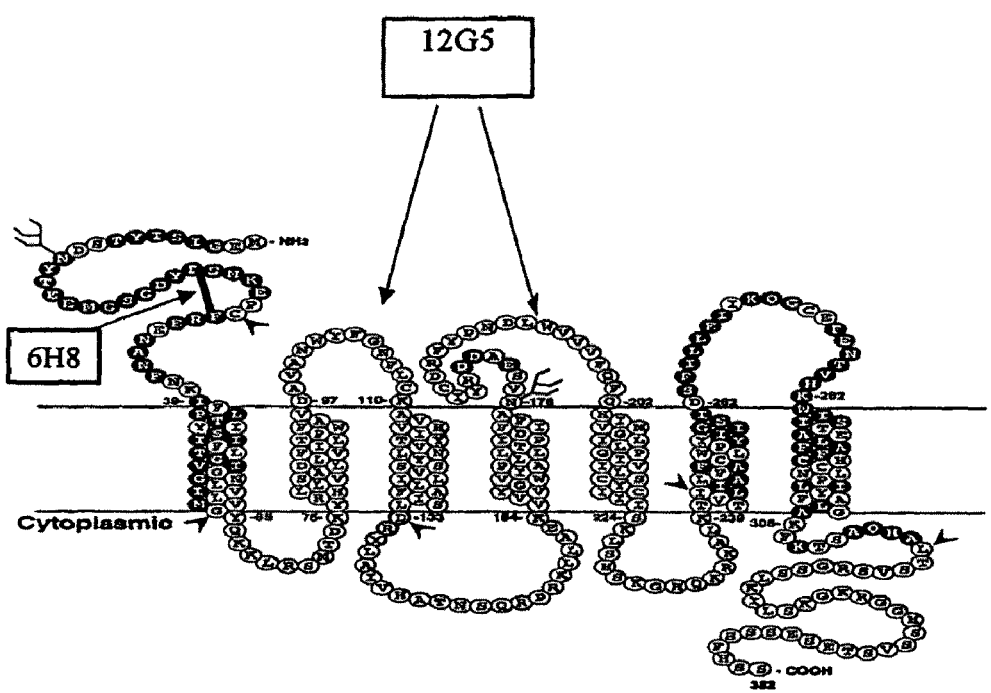
FIG. 7 shows a schematic illustration of CXCR4.

In a first set of experiments we analyzed the binding of the mAb 6H8, specific for residues 22-25 of human CXCR4-a site located within the first N-terminal extracellular domain of CXCR4 (FIG. 7), to either control GFP transduced cord blood CD34+ cells or CXCR4 overexpressing CD43+ cells. We found that GFP (control) transduced CB CD34+cells, expressing only endogenous CXCR4, failed to bind the mAb 6H8, despite binding the mAb 12G5 (not shown), which binds to the second extracellular domain of human CXCR4, whereas CXCR4 overexpressing CB CD34+ cells stained positive for both antibodies 12G5 and 6H8. These data suggest that overexpression of CXCR4 partially prevents deterioration or cleavage of the 6H8 epitope which has been shown to play a role in the CXCR4 chemotactic function (Brelot et al, J Biol. Chem. 275:23736-23744).

Figure 8:
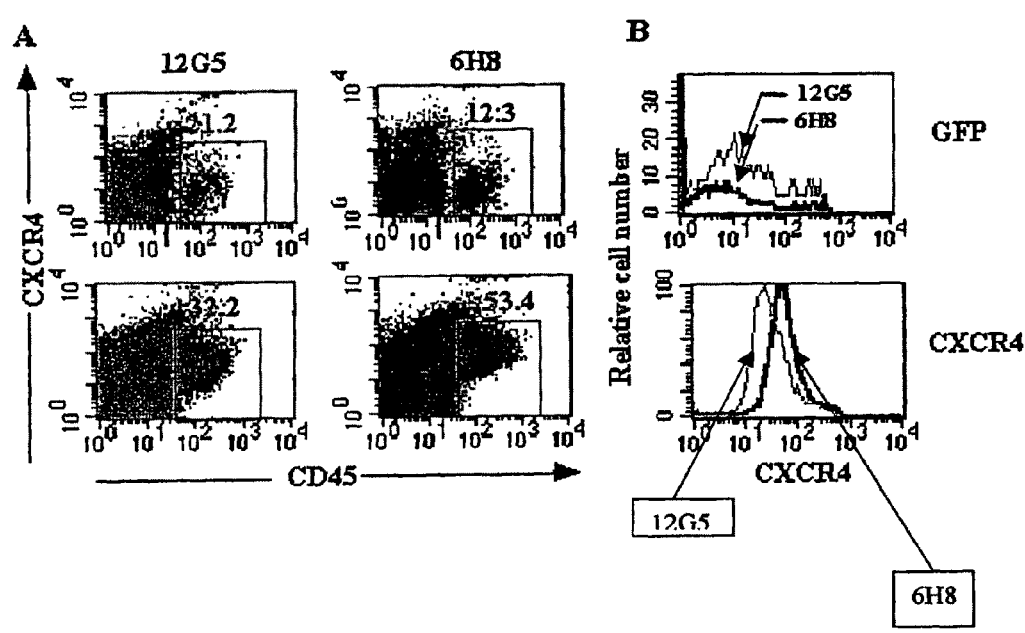
FIG. 8 shows that CXCR4 overexpression on CB CD34+ cells prevents deterioration of the 6H8 epitope in vivo. A. Transduced CD34+ cell were transplanted into sublethally (375R) irradiated NOD/SCID mice. Five weeks post transplantation, murine BM was harvested and analysed for the presence of human cells stained positive for the 12G5 or 6H8 epitope of CXCR4. Numbers represent mean CXCR4 fluorescence. B. Representative histogram FACS analysis of the mean CXCR4 fluorescence as in A following staining of GFP (control) and CXCR4 overexpessing cells with 12G5 and 6H8 mAbs.

In a second set of experiments, we followed the binding of 6H8 and 12G5 mAbs to human cells isolated from the BM of NOD/SCID mice transplanted with either control or CXCR4 overexpressing CB CD34+ cells (FIG. 8). We found that human cells isolated from chimeric murine BM, harboring human CXCR4 overexpressing cells, showed higher percentage of cells positive for both 6H8 and 12G5 than in chimeric marine BM harboring human control cells. Moreover, while control GFP bearing cells showed clear deterioration of the 6H8 epitope, there was no deterioration in GFP bearing CXCR4 overexpressing cells, indicating that there is also less deterioration in vivo of the 6H8 epitope in the overexpressing cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claim. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Morrison S J, Uchida N, Weissman I L. The biology of hematopoietic stem cells. Annu Rev Cell Dev Biol. 1995; 11:35
2. Abkowitz J, Robinson A, Kale S, Long M, Chen J. The mobilization of hematopoietic stem cells during homeostasis and after cytokine exposure. Blood. 2003
3. Wright D E, Wagers A J, Pathak Gulati A, Johnson F L, Weissman I L. Physiological migration of hematopoietic stem and progenitor cells. Science. 2001; 294:1933-1936
4. Selleri C, Maciejewski J, De Rosa G, Raiola A, Risitano A, Picardi M, Pezzullo L, Luciano L, Ricci P, Varriale G, Della Cioppa P, Del Vecchio L, Rotoli B. Long-lasting decrease of marrow and circulating long-term culture initiating cells after allogeneic bone marrow transplant. Bone Marrow Transplant. 1999; 23:1029-1037
5. Podesta M. Transplantation hematopoiesis. Curr Opin Hematol. 2001; 8:331-336.
6. Podesta M, Piaggio G, Frassoni F, Pitto A, Mordini N, Bregante S, Valeriani A, Bacigalupo A. Deficient reconstitution of early progenitors after allogeneic bone marrow transplantation. Bone Marrow Transplant. 1997; 19:1011-1017
7. Carton G, Herault O, Benboubker L, Clement N, Bernard M, Roingeard F, Desbois I, Colombat P. Binet C, Domenech J. Quantitive and qualitive analysis of the human primitive progenitor cell compartment after autologous stem cell transplantation. Journal of Hematotherapy & Stem Cell Research. 2002; 11:359-368
8. Hall K, Abonour R, Cometta K, EF S. Decreased homing of transduced human bone marrow CD34+ cells in NOD/SCID mice. Exp Hematol. 2003;abst. 100
9. Kang E, Hanazano Y, Frare P, Vanin E, De Witte M, Metzger M, Liu J, Tisdale J. Persistent low-level engraftment of rhesus peripheral blood progenitor cells transduced with the fanconi anemia C gene after conditioning with low-dose irradiation. Mol Ther. 2001; 3:911-919
10. Nagasawa T, Hirota S, Tachibana K, Takakura N, Nishikawa S, Kitamura Y, Yoshida N, Kikutani H, Kishimoto T. Defects of B-cell lymphopoiesis and bone-marrow myelopoiesis in mice lacking the CXC chemokine PBSF/SDF-1. Nature. 1996; 382:635-638
11. Ma Q, Jones D, Borghesani P R, Segal R A, Nagasawa T, Kishimoto T, Bronson R T, Springer T A. Impaired B-lymphopoiesis, myelopoiesis, and derailed cerebellar neuron migration in CXCR4- and SDF-1-deficient mice. Proc Nati Aced Sci USA. 1998; 959448-9453
12. Kollet O, Spiegel A, Peled A, Petit I, Byk T, Hershkoviz R, Quetta E, Barkai G, Nagler A, Lapidot T. Rapid and efficient homing of human CD34(+)CD38(–/low)CXCR4(+) stem and progenitor cells to the bone marrow and spleen of NOD/SCID and NOD/SCID/B2m(null) mice. Blood. 2001; 97:3283-3291
13. Paled A, Petit I, Kollet O, Magid M, Ponomaryov T, Byk T, Nagler A, Ben-Hur H, Many A, Shultz I., Lider O, Mon R, Zipori D, Lapidot T. Dependence of human stem cell engraftment and repopulation of NOD/SCID mice on CXCR4. Science. 1999; 283:845-848
14. Ponomaryov T, Peled A, Petit I, Taichman R, Habler L, Sandbank J, Arenzana-Seisdedos F, Magerus A, Caruz A, Fujii N, Nagler A, Lahav M, Szyper-Kravitz M, Zipori D, Lapidot T. Induction of the chemokine stromal-derived factor-I following DNA damage improves human stem cell function. JCI. 2000; 106:1331-1339
15. Kollet O, Petit I, Kahn J, Samira S, Dar A, Poled A, Deutsch V. Gunetti M, Piacibello W, Nagler A, Lapidot T. Human CD34+CXCR4– sorted cells harbor intracellular CXCR4, which can can be functionally expressed and provide NOD/SCID repopulation. Blood. 2002; 100

16. Spencer A, Jackson J, Baulch-Brown C. Enumeration of bone marrow 'homing' haemopoietic stem cells from G-CSF-mobilised normal donors and influence on engraftment following allogeneic transplantation. Bone Marrow Transplant. 2001; 28:1019-1022.

17. Voermans C, Kooi M L, Rodenhuis S, van der Lelie H, van der Schoot C E, Gerritsen W R. In vitro migratory capacity of CD34+ cells is related to hematopoietic recovery after autologous stem cell transplantation. Blood. 2001; 97:799-804

18. Lapidot T, Kollet O. The essential roles of the chemokine SDF-1 and its receptor CXCR4 in human stem cell homing and repopulation of transplanted immune-deficient NOD/SCID and NOD/SCID/B2m(null) mice. Leukemia. 2002; 16:1992-2003

19. Forster R, Kremmer E, Schubel A, Breitfeld D, Kleinschmidt A, Nerl C, Bernhardt G, Lipp M. Intracellular and surface expression of the HIV-1 coreceptor CXCR4/fusin on various leukocyte subsets: rapid internalization and recycling upon activation. J Immunol. 1998; 160:1522-1531

20. Kollet O, Shivtiel S. Chen Y Q, Suriawinata J, Thung S N, Dabeva M D, Kahn J, Spiegel A, Dar A, Samira S, Goichberg P, Kalinkovich A, Arenzana-Seisdedos F, Nagler A, Hardan I, Revel M, Shafritz D A, Lapidot T. HGF, SDF-1, and MMP-9 are involved in stress-induced human CD34+ stem cell recruitment to the liver. J Clin Invest. 2003;112:160-169

21. Rusten L, Cue L, Pharo A, Jacobsen S. Lapidot T, Kvalheim G. TNF-$\alpha$ and TGF-$\beta$ potently upregulate the expression of CXCR4 on peripheral blood progenitor cells. Blood. 2000;94:252a 22. Denning-Kendall P, Singha S, Bradley B, Hows J. Cytokine expansion culture of cord blood Cd34+ cells induces marked and sustained changes in adhesion receptor and CXCR4 expressions. Stem Cells. 2003; 21:61-70

23. Bhatia M, Wang J C Y, Kapp U, Bonnet D, Dick J E. Purification of primitive human hematopoietic cells capable of repopulating immune-deficient mice. Proc Natl Aced Sci USA. 1997; 94:5320-5325

24. Wright D E, Bowman E P, Wagers M, Butcher E C, Weissman I L. Hematopoietic stem cells are uniquely selective in their migratory response to chemokines. J Exp Med. 2002; 195:1145-1154

25. Grafte-Faure S. Levesque C, Ketata E, Jean P, Vasse M, Soria C, Vannier J P. Recruitment of primitive peripheral blood cells: synergism of interleukin 12 with interleukin 6 and stromal cell-derived FACTOR-1. Cytokine. 2000; 12:1-7

26. Broxmeyer H E, Hangoc G, Cooper S, H. K C. Enhanced myelopoiesis in sdf-1-transgenic mice: sdf-1 modulates myelopoeisis by regulating progenitor cell survival and inhibitory effects of myelosuppresive chemokines [abstract]. Blood. 1999; 94:650a 27. Lataillade J J, Clay D, Dupuy C, Rigel S, Jasmin C, Bourin P, Le Bousse-Kerdiles M C. Chemokine SDF-1 enhances circulating CD34(+) cell proliferation in synergy with cytokines: possible role in progenitor survival. Blood. 2000; 95:756-768

28. Lataillade J J, Clay D, Bourin P. Herodin F, Dupuy C, Jasmin C, Bousse-Kerdiles M C. Stomal cell-derived factor 1 regulates primitive hematopoiesis by suppressing apoptosis and by promoting G(0)/G(1) transition in CD34(+) cells: evidence for an autocrine/paracrine mechanism. Blood. 2002; 99:1117-1129.

29. Broxmeyer H, Kohli L, Kim C, Lee Y, Mantel C, Cooper S, Hangoc G, Shaheen M, Li X, Clapp D. Stromel cell-derived factor-1/CXCL12 directly entmaces survival/antiapoptosis of myeloid progenitor cells through CXCR4 and G$\alpha$i proteins and enhances engraftment of competitive, repopulating stem cells. J. Leukoc. Biol. 2003; 73:630-638

30. Cashman J, Clark-Lewis I, Eaves A, Eaves C. Stromalderived factor 1 inhibits the cycling of very primitive human hematopoietic cells in vitro and in NOD/SCID mice. Blood. 2002; 99:792-799.

31. Cashman J, Dykstra B, Clark-Lewis I, Eaves A, Eaves C. Changes in the proliferative activity of human hematopoietic stem cells in NOD/SCID mice and enhancement of their transplantibility after in vivo treatment with cell cycle inhibitors. J. Exp. Med. 2002; 196:1141-1149

32. Ma Q, Jones D, Springer T A. The chemokine receptor CXCR4 is required for the retention of B lineage and granulocytic precursors within the bone marrow microenvironment. Immunity. 1999; 10:463-471

33. Kawabata IC, Ujikawa M, Egawa T, kawamoto H, Tachibana K, Iizasa H, Katsura Y, kishimoto T, Nagasawa T. A cell-autonomous requirement for CXCR4 in long-term lymphoid and myeloid reconstitution. Proc. Natl. Acad. Sci. USA. 1999; 96:5663-5667

34. Yahata T, Ando K, Sato T, Miyatake H, Nakamura Y, Mugurumu Y, Kato S, Hotta T. A highly sensitive strategy for SCID-repopulating cell assay by direct injection of primitive human hematopoietic cells into NOD/SCID mice bone marrow. Blood. 2003; 101:2905-2913

35. Wang J, Kimura T, Asada R, Harada S. Yokota S, Kawamota Y, Fujimura Y, Tsuji T, Ikehara S. Sonoda Y. SCID-repopulating cell activity of human cord blood-derived CD34– cells assured by intra-bone marrow injection. Blood. 2003; 101:2924-2931

36. Shen H, Cheng T, Olszak I, Garcia-Zepeda E, Lu Z, Herrmann S, Fallon R, Luster A D, Scadden D T. CXCR-4 desensitization is associated with tissue localization of hemopoietic progenitor cells. J Immunol. 2001; 166:5027-5033

37. Sweeney E A, Lortat-Jacob H, Priestley G V, Nakamoto B, Papayannopoulou T. Sulfated polysaccharides increase plasma levels of SDF-1 in monkeys and mice: involvement in mobilization of stem/progenitor cells. Blood. 2002; 99:44-51

38. Levesque J-P, Bendall L J, Hendy J, Williams B, Simmons P J. SDF-1$\alpha$ is inactivated by proteolytic cleavage in the bone marrow of mice mobilized by either G-CSF or cyclophosphamide. Blood. 2001; 98:831a 39. Moore M A, Hattori K, Heissig B, Shieh Dias S, Crystal R G, Rafii S. Mobilization of endothelial and hematopoietic stem and progenitor cells by adenovector-mediated elevation of serum levels of SDF-1, VEGF, and angiopoietin-1. Ann. N. Y. Acad. Sci. 2001; 938:36-45, 45-37

40. Hattori K, Heissig B, Tashiro K, Honjo T, Tateno M, Shieh J H, Hackett N R, Quitoriano M S, Crystal R G, Rafii S, Moore M A. Plasma elevation of stromal-derived factor-1 induces mobilization of mature and immature hematopoietic progenitor and stem cells. Blood. 2001; 97:3354-3360

41. Petit I, Szyper-Kravitz M, Nagler A, Lahav M, Peled A, Habler L, Ponomaryov T, Taichman R S, Arenzana-Seisdedos F, Fujii N, Sandbank J, Zipori D, Lapidot T. G-CSF induces stem cell mobilization by decreasing bone marrow SDF-1 and up-regulating CXCR4. Nat Immunol. 2002; 3:687-694

42. Sawada S, Gowrishanlcar K, Kitamura R, Suzuki M, Suzuki G, Tahara S, Koito A. Disturbed CD4+ T cell homeostasis and in vitro HIV-1 susceptibility in transgenic mice expressing T cell line-tropic HIV-1 receptors. J. Exp. Med. 1998; 187:1439-1449

43. Guenechea G, Gan O I, Inamitsu T, Dorrell C, Pereira D, Kelly M, Naldini L, Dick J. Transduction of human CD34+

44. Miyoshi H, Smith K, Mosier D, Verma I, Torbett B. Transduction of human CD34+ cells that mediate long-term engraftment of NOD/SCID mice by HIV vectors. Science. 1999; 283:682-686

45. Barquinero J, Segovia J, Ramirez M, Limon A, Guenechea G, Puig T, Briones J, Garcia J, Bueren J. Efficient transduction of human hematopoietic repopulating cells generating stable engraftment of transgene-expressing cells in NOD/SCID mice. blood. 2000:3085-3093

46. Woods N, Fahlman C, Mikkola H, Hamaguchi I, Olsson K, Zufferey R, Jacobsen S, Trono D, Karlsson S. Lentiviral gene transfer into primary and secondary NOD/SCID repopulating cells. Blood. 2000; 96:3725-3733

47. Sutton R, Reitsma M, Uchida N, Brown P. Transduction of human progenitor hematopoietic stem cells by human immunodeficiency virus type 1-based vectors is cell cycle dependent. J Virol. 1999; 73:3649-3660

48. Cavazzana-Calvo M, Hacein-Bey S, Basile G. Gene therapy of human severe combined immunodeficiency (SCID)-X1 disease. Science. 2000; 288:669-672

49. Aiuti A, Slavin S, Aker M, Ficara F, Deola S. Morteellaro A, Morecki S, Andolfi G, Tabucchi A, Carlucci F, Marinello E, Cattaneo F, Vai S, Servida P, Miniero R, Roncarolo M, Bordignon C. Correction of ADA-SCID by stem cell gene therapy combined with nonmyeloblative conditioning. Science. 2002; 296:2410-2413

50. Darash-Yahana M, Kahn J, Asian H, Gropp M, Nagler A, Gazit Z, Reubinoff B, Lapidot T, Gazit D, Galun E, Peled A. Rapid and efficient lentiviral mediated transduction of human mesenchymal and hematopooietic stem cells. Submitted. 2003

51. Wagstaff M, Lilley C, Smith J, Robinson M, Coffin B. Latchman D. Gene transfer using a disabled herpes virus vector containing the EMCV IRES allows multiple gene expression in vitro and in vivo. Gene Thor. 1998; 5:1566-1570

52. Metcalf D. Haemopoietic colonies: In vitro cloning of normal and leukemic cells. Recnt Results in Cancer Res. 1977; 61:1

53. Gibellini D, Bassini A, Re M C, Ponti C, Miscia S. Gonelli A, La Placa M, Zauli G. Stroma-derived factor 1alpha induces a selective inhibition of human erythroid development via the functional upregulation of Fas/CD95 ligand. Br J Haematol. 2000; 111:432-440

54. Bleul C C, Aiuti A, Fuhlbrigge R C, Casasnovas J M, Springer T A. A highly efficacious lymphocyte chemoattractant, stromal cell-derived factor 1 (SDF-1). The Journal of Experimental Medicine. 1996; 184:1101-1109

55. Signoret N, Oldbridge J, Perchen-Matthews A, Klasse P J, Tran T, Brass L F, Rosenkilde M M, Schwartz T W, Holmes W, Dallas W, Luther M A, Wells T N, Hoxie J A, Marsh M. Phorbol esters and SDF-1 induce rapid endocytosis and down modulation of the chemokine receptor CXCR4. J. Cell Biol. 1997; 139:651-664

The invention claimed is:

1. An isolated population of human cord blood or bone marrow stem cells comprising a transgene encoding CXCR4, wherein the stem cells are resistant to desensitization by high concentrations of SDF-1 as compared to stem cells lacking the transgene encoding CXCR4, and wherein the CXCR4 is a naturally occurring CXCR4.

2. The isolated population of stem cells according to claim 1, wherein the stem cells are hematopoietic stem cells.

3. The isolated population of stem cells according to claim 1, wherein the stem cells are capable of differentiating towards the myeloid and erythroid lineages.

4. The isolated population of stem cells according to claim 3, wherein the stem cells are CD34$^+$ hematopoietic stem cells.

5. The isolated population of stem cells according to claim 1, wherein the stem cells are CD34$^+$/CD38$^{-/low}$ cells.

6. The isolated population of stem cells according to claim 3, wherein the high amount of CD34$^+$/CD38$^{-/low}$ cells is about 1-5% of the population.

7. The isolated population of stem cells according to claim 3, wherein the high amount of CD34$^+$/CD38$^{-/low}$ cells is at least 3% of the population.

8. The isolated population of stem cells according to claim 1, wherein the low concentration of SDF-1 is less than or equal to 50 ng/ml.

9. The isolated population of stem cells according to claim 1, wherein the high concentration of SDF-1 is at least 1 microgram/ml.

10. A method for increasing homing of stem cells to a target tissue in a subject in need thereof, comprising administering to said subject a population of cells according to claim 1.

11. A method for increasing repopulation of a target tissue in a subject in need thereof, comprising administering to said subject a population of cells according to claim 1.

12. The method according to claims 10, wherein said target tissue is selected from the group consisting of bone marrow, blood vessel, heart, lung, liver, pancreas, kidney, nervous system, skin, bone and skeletal muscle.

13. A method for transplantation in a subject in need thereof, comprising contacting said subject with the population of cells according to claim 1.

14. The method according to claim 13, wherein transplantation follows chemotherapy protocols.

15. The method according to claim 13, wherein transplantation is autologous.

16. The method according to claim 15, wherein the transplantation involves mobilization of autologous cells.

17. The method according to claim 13, wherein transplantation is heterologous.

18. The method according to claim 13, wherein the transplantation is carried with mobilized stem cells.

19. A method of treating a disorder in a subject requiring cell or tissue replacement, the method comprising providing to a subject in need thereof a therapeutically effective amount of a population of cells according to claim 1.

20. A method of preparing a population of stem cells exhibiting CXCR4 with intact 6H8 epitope, the method comprising collecting stem cells according to claim 1.

21. A population of stem cells comprising a transgene expressing an increased level of a naturally occurring CXCR4 comprising an intact CXCR4 6H8 epitope as compared to stem cells lacking the transgene encoding CXCR4.

22. A method for transplantation in a subject in need thereof, comprising contacting said subject with the population of cells of claim 21.

23. A pharmaceutical composition comprising stem cells according to claim 21.

24. The isolated population of stem cells according to claim 5, wherein the high amount of CD34$^+$/CD38$^{-/low}$ cells is about 3% of the population.

25. An isolated population of human cord blood or bone marrow stem cells comprising a transgene encoding CXCR4, wherein the CXCR4 is expressed at a level conferring resistance to desensitization by high concentrations of SDF-1 as compared to stem cells lacking the transgene encoding CXCR4, and wherein the CXCR4 is a naturally occurring CXCR4.

26. An isolated population of human cord blood or bone marrow stem cells comprising a transgene encoding CXCRb 4, wherein the CXCR4 is expressed at a level providing increased intact CXCR4 as compared to stem cells lacking the transgene encoding CXCR4, and wherein the CXCR4 is a naturally occurring CXCR4.

* * * * *